(12) United States Patent
Kyndt et al.

(10) Patent No.: US 7,241,611 B2
(45) Date of Patent: Jul. 10, 2007

(54) METHODS FOR SYNTHESIS OF HOLO-PHOTOACTIVE YELLOW PROTEIN

(75) Inventors: John Jozef Armand Kyndt, Harelbeke (BE); Jozef Van Beeumen, Merelbeke (BE)

(73) Assignee: Universiteit Gent, Ghent (BE)

( * ) Notice: Subject to any disclaimer, the term of this patent is extended or adjusted under 35 U.S.C. 154(b) by 552 days.

(21) Appl. No.: 10/464,609

(22) Filed: Jun. 18, 2003

(65) Prior Publication Data

US 2004/0029230 A1    Feb. 12, 2004

Related U.S. Application Data

(60) Provisional application No. 60/389,593, filed on Jun. 18, 2002.

(51) Int. Cl.
*C12P 7/40* (2006.01)
*C12N 9/88* (2006.01)
*C12N 1/21* (2006.01)
*C07H 21/04* (2006.01)

(52) U.S. Cl. .................. 435/252.3; 435/136; 435/69.1; 435/320.1; 435/232; 435/325; 536/23.2

(58) Field of Classification Search ................ 435/232, 435/146
See application file for complete search history.

(56) References Cited

U.S. PATENT DOCUMENTS 6,368,837 B1 * 4/2002 Gatenby et al. ............ 435/146
6,951,751 B2 * 10/2005 Breinig et al. .............. 435/232

OTHER PUBLICATIONS

Kyndt et al Feb. 13, 2002, FEBS Lett. 512, pp. 240-244.*

* cited by examiner

*Primary Examiner*—Rebecca E. Prouty
*Assistant Examiner*—M. Y. Meah
(74) *Attorney, Agent, or Firm*—Clark & Elbing LLP

(57) ABSTRACT

The present invention is generally related to recombinant DNA technology and more particularly to DNA strands useful for the production of parahydroxycinnamic acid and photoactive yellow protein in a suitable host expression system.

20 Claims, 13 Drawing Sheets

METHODS FOR SYNTHESIS OF HOLO-PHOTOACTIVE YELLOW PROTEIN

This application claims the benefit of U.S. Provisional Application No. 60/389,593, filed Jun. 18, 2002, the disclosure of which is hereby incorporated by reference.

FIELD OF THE INVENTION

The present invention is generally related to recombinant deoxyribonucleic acid (DNA) technology and more particularly to DNA strands useful for the biosynthetic pathway of the photoactive yellow protein in *Escherichia coli* or in microorganisms into which the DNA strands have been introduced.

BACKGROUND TO THE INVENTION

The photoactive yellow protein (PYP) is a small cytoplasmatic protein capable of performing a photocycle when illuminated with blue light (λ max=446 nm). PYP has already been intensively studied with respect to its structural and biophysical features by several research groups (Borgstahl et al, 1995; Ujj et al, 1998; Perman et al., 1998; Genick et al., 1998). These studies have shown that this photoreceptor is a very good model to investigate the mechanism of light perception in biological systems. The chromophore of PYP is p-hydroxycinnamic acid, bound to a cysteine via a thioester bond. Upon illumination, PYP undergoes a photocycle which involves a trans-to-cis isomerisation of the chromophore. Analogous photocycles, although with a different chromophore, have been detected in e.g. bacteriorhodopsin, halorhodopsin, and the sensory rhodopsins (SRI and SRII) from *Halobacterium salinarum*. Several intermediates of the photocycle have been characterized, both photochemically and structurally. The PYP was first isolated from *Halorhodospira halophila* (Meyer, 1985). The similarity between the visible absorption spectrum of PYP and the wavelength dependence of the negative phototactic response implies PYP to be the receptor responsible for this effect (Sprenger et al., 1993). The protein was also found in *Rhodospirillum salexigens* and *Halochromatium salexigens* (Koh et al., 1996). Pyp-homologous genes were found in *Rhodobacter sphaeroides* (Kort et al., 1996) and *Rhodobacter capsulatus* (www.integratedgenomics.com). In *Rhodospirillum centenum*, a PYP-phytochrome chimera has been isolated, which is presumably involved in the regulation of the enzyme chalcone synthase (Jiang et al., 1999).

The biosynthetic pathway of p-hydroxycinnamic acid has been intensively studied in plants (Hahlbrock and Scheel, 1989; Dixon and Pavia, 1995; Campbell et al., 1996), in which trans-cinnamic acid is synthesized from L-phenylalanine by the action of a phenylalanine ammonia lyase (PAL). In the presence of a P450 enzyme system, t-cinnamic acid can be converted to p-hydroxycinnamic acid. Subsequently in this so-called 'phenylpropanoid pathway', the p-hydroxycinnamic acid is linked to coenzyme A by a p-hydroxycinnamyl:CoA ligase (pCL). The product formed in this pathway serves as an intermediate in plants for the production of various secondary metabolites, such as lignin and isoflavonoids.

Not only has PAL activity been found in plants (Koukol et al., 1961), it was also detected in fungi (Bandoni et al., 1968), yeast (Ogata et al., 1967) and *Streptomyces* (Emes et al., 1970). The gene sequence of pal from various sources has been determined and published (Edwards et al., 1985; Cramer et al., 1989; Louis et al., 1989; Minami et al., 1989; Anson et al., 1987, Rasmussen and Oerum, 1991). Studies of PAL from plants and micro-organisms have indicated that, in addition to its ability to convert L-phenylalanine to cinnamic acid, it can also accept L-tyrosine as a substrate. In these reactions the p-hydroxycinnamic acid is directly formed from L-tyrosine, without the formation of trans-cinnamic acid and without the intervention of a P450 enzyme system. In this case the enzyme is referred to as a tyrosine ammonia lyase (TAL). However, all eukaryotic PAL/TAL enzymes prefer the use of L-phenylalanine rather than L-tyrosine as their substrate. The level of TAL activity is always lower than PAL activity, but the magnitude of this difference varies over a wide range. As pointed out by Rösler et al. (1997), PAL and TAL activities reside on the same polypeptide in monocotylic plants. Both activities have similar catalytic efficiencies, in spite of large differences in $K_M$ and turnover numbers. The enzyme from dicotyledonous plants, on the other hand, only uses L-phenylalanine efficiently. Related to this enzyme an application was filed by Dupont (WO 02/10407 A1), entitled: 'Bioproduction of para-hydroxycinnamic acid'. In essence, the construction of a TAL enzyme by mutagenesis of the yeast *Rhodotorula glutinis* PAL/TAL enzyme and production of the enzyme in *Escherichia coli* is claimed. The ratio of TAL activity to PAL activity is described to be 1.7.

No information was known about the occurrence of this enzyme in eubacteria, until we recently cloned and expressed a tyrosine ammonia lyase from *Rhodobacter capsulatus* (Kyndt et al, 2002). As described below, we showed that the catalytic efficiency of the *Rhodobacter* TAL for L-tyrosine was approximately 150 times larger than for L-phenylalanine under physiological conditions. This is the first enzyme that was found to have a larger specificity for L-tyrosine as substrate than for L-phenylalanine. After DNA sequencing it was found that there are four basepair differences, resulting in two differences in the translated protein sequence (His522→Asp and Ala535 deletion), as compared to the gene found in the *Rhodobacter capsulatus* genome sequencing project (www.integratedgenomics.com). We attributed these differences to either strain differences or genome sequencing errors. In the genome sequencing project the sequence in question is annotated as being a PAL, based on sequence homology.

pCL-activity has been found in several plants (e.g., Gross and Zenk, 1966; Lindl et al., 1972; Knobloch and Hahlbrock, 1977; Ehlting et al., 1999; Obel and Scheller, 2000). The enzyme catalyses the activation of various hydroxylated and methoxylated cinnamic acid derivatives to the corresponding thiol esters in a two-step reaction. During the first step, the coumaric acid and ATP form a coumaroyl-adenylate intermediate with the simultaneous release of pyrophosphate. In the second step, the coumaroyl group is transferred to the sulfhydryl group of CoA, and AMP is released. Despite their low overall sequence identity, one highly conserved peptide motif is common to pCLs, luciferases, fatty acyl-CoA synthetases and acetyl-CoA synthetases. This conserved, putative AMP binding domain has been used as the most important criterion to group these proteins in one superfamily, that of the adenylate-forming enzymes (Fulda et al., 1994).

Bacterial genes homologous to this second enzyme (pCL) were found downstream of the pyp gene in *Halorhodospira halophila* and *Rhodobacter sphaeroides* (Kort et al., 1996; Kort et al., 1998). During the sequencing of the *Rhodobacter capsulatus* genome a pcl homologous ORF was found (www.integratedgenomics.com). None of the gene products of these bacterial pcl sequences have been characterised, so it is not yet established whether or not coenzyme A is also the thiol containing substrate for the bacterial pCLs. Kort et al. (1996) suggested that "the pcl homologous gene product could be involved in an activation of the chromophore by the formation of a thioester bond with Coenzyme A". He also suggested that the biosynthesis of p-coumaric acid, which in plants is performed by PAL, may consist of three consecutive steps in prokaryotes. If so, it was speculated that an aromatic aminotransferase, a 2-keto-acid reductase and a dehydratase, respectively, would be involved.

The present inventors have made it possible to clone and express the two biosynthetic genes (tal and pcl) of the photosynthetic bacteria Rhodobacter capsulatus in Escherichia coli. Until now, the only possible way to produce recombinant holo-PYP was to chemically attach the chromophore to the recombinant apo-PYP, as described by Imamoto et al. (1995) and Genick et al. (1997). The latter method was shown to have a lower yield of holo-PYP and may lead to non-specific reactions as compared to the present invention. We also found that the chemical reconstitution method failed when attempting to produce recombinant holo-PYP from Rhodobacter capsulatus, whereas the present invention is able to produce the holo-protein in large amounts.

The PYP cannot be produced in large amounts in natural genera, nor does the heterologous expression of the pyp gene alone in Escherichia coli and Rhodobacter sphaeroides lead to the formation of holo-PYP (Kort et al., 1996).

SUMMARY OF THE INVENTION

The present invention relates to a recombinant vector comprising a gene encoding a tyrosine-ammonium lyase (TAL) polypeptide having a catalytic efficiency for L-tyrosine which is at least 10 times higher for L-tyrosine than for L-phenylalanine, for use in the production of para-hydroxycinnamic acid and derivative products thereof, such as holo-photoactive yellow protein.

It is the first object of this invention to clone and express in a host cell (such as, but not limited to Escherichia Coli or other microorganisms) the biosynthetic pathway of the photoactive yellow protein, in order to produce the photoactive holo-PYP in high internal concentrations.

Accordingly, the present invention provides a method for synthesis of holo-photoactive yellow protein which comprises introducing a gene encoding a tyrosine-ammonium lyase (TAL) polypeptide and a gene encoding a p-hydroxycinnamyl:CoA ligase (pCL) polypeptide into a host expression system, said host expression system being capable of producing apo-PYP, culturing said host expression system under conditions allowing the expression of said TAL, pCL and apo-PYP, and optionally, recovering said holo-active protein.

More particularly, the present invention provides a method for in vivo synthesis of holo-photoactive yellow protein comprising the steps of:
(a) providing a first construct, said first construct comprising a dual biosynthetic gene operon consisting essentially of:
a tyrosine ammonia lyase gene; and
a p-hydroxycinnamyl:CoA ligase gene;
wherein said genes are operably linked to a suitable regulatory sequence;
(b) providing a second construct, said second construct comprising a further biosynthetic gene, said further biosynthetic gene being a photoactive yellow protein,
wherein said photoactive yellow protein is operably linked to a suitable regulatory sequence;
(c) introducing said first and second constructs into a host expression system;
(d) culturing said host expression system under conditions allowing expression of said biosynthetic genes; and
(e) recovering holo-photoactive yellow protein.

According to a second aspect of the present invention, enzymes have been cloned from a eubacterium, which are involved in the production of photoactive yellow protein (PYP). More particularly, a tyrosine ammonia lyase (TAL) has been cloned from Rhodobacter capsulatus which has a catalytic efficiency for L-tyrosine which is approximately 150 times higher than for L-phenylalanine under physiological conditions. Thus, this aspect of the invention relates to bacterial tyrosine ammonia lyase enzymes, which have a higher efficiency for L-tyrosine than for L-phenylalanine. This enzyme is particularly suited for the production of para-hydroxycinnamic acid and molecules, the production of which involves para-hydroxycinammic acid, such as, but not limited to, holo-PYP.

The invention further relates to bacterial enzymes with p-hydroxycinnamyl:CoA ligase (pCL) activity. More particularly, a pCL has been cloned from a bacterium, more particularly from Rhodobacter capsulatus. According to the present invention, expression of the bacterial TAL and pCL of the present invention in combination with a sequence encoding PYP, allows high level production of holo-PYP.

DETAILED DESCRIPTION OF THE INVENTION

'Photoactive yellow protein' or 'PYP' as used herein relates to a cytoplasmatic protein capable of performing a photocycle when illuminated with blue light ($\lambda$ max=446 nm). A pyp gene as used herein refers to a DNA strand or nucleotide sequence encoding a PYP. According to a preferred embodiment of the invention, PYP is encoded by a pyp gene from Halorhodospira halophila, but alternative pyp genes include but are not limited to pyp genes from Rhodospirillum salexigens or Halochromatium salexigens, Rhodobacter sphaeroides or Rhodobacter capsulatus. Even further alternative PYP proteins include the Ppr (PYP phytochrome related) proteins such as those identified from Rhodospirillum centenum. According to a preferred embodiment of the present invention, PYP is a protein encoded by the sequence as described in SEQ ID NO: 1, a fragment thereof, or a sequence having at least 85%, more preferably at least 90%, especially preferably at least 95%, most preferably 98% sequence identity with the sequence of SEQ ID NO:1, and encoding a photoactive protein or polypeptide. According to another embodiment of the present invention, PYP relates to an amino acid sequence of SEQ ID NO: 2, a fragment thereof, or a sequence having at least 85% sequence identity therewith, having PYP activity. 'Holo-PYP' is used to emphasize the presence of the chromophore and thus is also used to refer to the photo-active protein as opposed to apo-pyp, which is used to refer to the sequence of PYP without the chromophore.

'Tyrosine ammonia lyase' or 'TAL' enzyme as used herein relates to a biosynthetic protein or polypeptide which converts L-tyrosine to para-hydroxycinnamic acid. More particularly, such a TAL enzyme in the context of the present invention is a bacterial enzyme which has a higher catalytic efficiency (as can be determined from Kcat/Km values) with L-tyrosine than with L-phenylalanine as a substrate, preferably the efficiency for L-tyrosine is 10 times higher than for phenylalanine, more preferably, 50 times higher, most preferably 100 to 150 times higher. Such a difference in efficiency is preferably measured under physiological conditions, i.e. conditions that generally correspond to a salt concentration of 7-10 g/L, a pH of 6-8 and temperature between 20°-40° C. Preferably, the affinity for L-tyrosine of the TAL polypeptide according to the present invention is at least 5 times, preferably at least 10 times, most preferably at least 50 times, especially preferably 80 times higher than for L-phenylalanine (as can be deduced from the Km value). According to a particular embodiment of the present invention, a TAL polypeptide is a polypeptide encoded by SEQ ID NO: 3 or a fragment thereof having at least 85%, more preferably at least 90%, especially preferably at least 95%, most preferably 98% sequence identity with the sequence of SEQ ID NO: 3, encoding a protein or polypeptide having TAL activity. According to another embodiment of the present invention, a TAL polypeptide is a polypeptide having the amino acid sequence of SEQ ID NO: 4, a sequence having at least 85% sequence identity with SEQ ID NO: 4 or a fragment thereof, having TAL activity. A 'tal gene' as used herein, refers to a nucleotide sequence encoding a TAL as defined herein.

'p-hydroxycinnamyl:CoA ligase' or 'pCL' as used herein refers to an enzyme capable of linking p-hydroxycinnamic acid to a thiol containing component, such as, but not limited to coenzyme A, gluthation, or cysteine. According to the present invention, nucleotide sequences encoding pCL are used in the biosynthetic pathway of proteins, such as, but not limited to, holo-PYP, and can be obtained from plants or bacteria. Plant pCL enzymes capable of linking p-hydroxycinnamic acid to coenzyme A have been described in the art. According to a particular embodiment bacterial pCL enzymes are provided, more particularly a pCL encoded by a gene cloned from *Rhodobacter capsulatus*, or a polypeptide encoded by the sequence of SEQ ID NO: 5 or a fragment thereof having at least 85%, more preferably at least 90%, especially preferably at least 95%, most preferably 98% sequence identity with the sequence of SEQ ID NO: 5, encoding a protein or polypeptide having pCL activity. According to another embodiment of the present invention, a pCL polypeptide is a polypeptide having the amino acid sequence of SEQ ID NO: 6, or a sequence having at least 85% sequence identity with SEQ ID NO: 6 or a fragment thereof, having pCL activity. A 'pcl gene' as used herein, refers to a nucleotide sequence encoding a pCL as defined herein.

The term "gene" as used herein refers to any DNA sequence comprising several operably linked DNA fragments such as a promoter region, a 5' untranslated region (the 5'UTR), a coding region, and an untranslated 3' region (3'UTR) comprising a polyadenylation site. Typically the 5'UTR, the coding region and the 3'UTR are transcribed into an RNA of which, in the case of a protein encoding gene, the coding region is translated into a protein. A gene may include additional DNA fragments such as, for example, introns. When referring to a 'pyp gene', a 'tal gene' or a 'pCL gene' herein in the context of expression in a host organism, it is understood that such genes include, in addition to the nucleotide sequences encoding the PYP, TAL and pCL polypeptides, suitable regulatory regions for expression in such a host organism as are known in the art.

While the invention has mostly been described in terms of cloning the holo-PYP biosynthetic pathway from a specific bacterium into *Escherichia coli*, it is clear that other microorganisms can be used for the expression of the biosynthetic genes, in a manner contemplated within the spirit and scope of the appended claims.

By the use of PCR, a gene from *Rhodobacter capsulatus* that was annotated during the genome-sequencing project as coding for a phenylalanine ammonia lyase was isolated (see SEQ ID NO: 3). The gene was cloned into an expression vector for *Escherichia coli*. Two differences were found in the translated amino acid sequence as compared to what was published by the genome-sequencing project. After purification and enzymatic characterisation of the encoded protein (see SEQ ID NO: 4), the enzyme was shown to have at least a 150 times higher specificity for L-tyrosine than for L-phenylalanine. Therefore we believe the enzyme to be the first bacterial tyrosine ammonia lyase, instead of a phenylalanine ammonia lyase (Kyndt et al., 2002).

A second gene was isolated from *Rhodobacter capsulatus* by the use of PCR. In this case the sequence was annotated, based on sequence homology, as coding for a p-hydroxycinnamyl:CoA ligase. Analogous to the tal gene, the pcl gene was cloned into an expression vector for *Escherichia coli*.

According to the present invention tal and pcl genes can be cloned into an expression vector for expression either alone, or together with other introduced nucleotide sequences, in a suitable host. More particularly, within the context of the present invention, production of holo-PYP is envisaged, by expression of tal and pcl genes in combination with a nucleotide sequence encoding PYP. According to the present invention, both tal and pcl were recloned into a vector compatible to most of the commercially available expression vectors for *Escherichia coli*. After introduction with an additional plasmid comprising the gene coding for apo-PYP, a system was developed for the production of reconstituted and photoactive holo-PYP in *Escherichia coli* up to levels of 60-80 mg per liter of culture.

Thus, the present invention describes a process for producing the holo-photoactive yellow protein, as set forth below:

A process of producing holo-PYP comprising the introduction of the following DNA strands:

a DNA strand from *Rhodobacter capsulatus* or another bacterial organism, having a nucleotide sequence which encodes a polypeptide having an enzymatic activity for converting L-tyrosine to p-hydroxycinnamic acid, by the elimination of ammonia; and a DNA strand from *Rhodobacter capsulatus* having a nucleotide sequence which encodes a polypeptide having an enzymatic activity for linking p-hydroxycinnamic acid to Coenzyme A, or some other thiol containing component, via a thioester linkage;

into a host system having the ability of synthesizing apo-PYP, culturing subsequently said host system in a culture medium and obtaining high amounts of photoactive holo-PYP from the cultured cells.

A host system having the ability of synthesizing apo-PYP can be either a host system in which the PYP protein is naturally expressed, or a host system into which a DNA strand encoding PYP is introduced (before, after or simultaneously with the introduction of the DNA strands encoding polypeptides with TAL and pCL activity, respectively).

The above-mentioned DNA strands may be introduced into said host system by way of transformation, transfection or transduction, as well known by a person skilled in the art, said way of introduction being dependent on, among others, the host system used.

The terms "construct", "plasmid", and "vector" are used interchangeably throughout the present invention and relate to independently replicating extrachromosomal cytoplasmic DNA that can be introduced into an organism. A construct in itself may also reside in an organism. Said extrachromosomal cytoplasmic DNA may be linear or circular DNA molecules found in both pro and eukaryotes capable of autonomous replication. Different vectors may have properties particularly appropriate to give protein expression in the recipient or host system or for cloning or may have different selectable markers. Constructs, plasmids, or vectors may be recombinant DNA systems especially suited for production of large quantities of specific proteins in e.g., bacterial, yeast, plant, insect, or mammalian cell systems. A recombinant vector is a vector which is the result of genetic engineering, i.e. not a naturally occurring vector.

In a suitable example, the above-mentioned DNA strands may be introduced into said host system by transformation, including co-transformation or transfection, including co-transfection by a construct comprising a dual biosynthetic gene operon, wherein expression of said DNA strands is under control of a single regulatory sequence in a single operon. Alternatively, each DNA strand may be under control of a separate regulatory sequence, in separate operons, said operons may be present on a single construct or not.

In order to clone and express in a host system such as e.g., a micro-organism, the biosynthetic pathway of the photoactive yellow protein to produce photoactive holo-PYP according to the present invention, a tyrosine ammonia lyase gene (tal), a p-hydroxycinnamyl:CoA ligase gene (pcl) and (optionally) a photoactive yellow protein gene (pyp) are expressed in said micro-organism. Optionally, tal and pcl can be introduced into a host system capable of expressing pyp. Such a host system can either naturally express pyp and/or can express pyp as a result of the introduction of a gene encoding PYP. As mentioned above, said tal and pcl gene sequences may be introduced on one construct or may be introduced on separate compatible constructs. Furthermore, tal, pcl, and pyp sequences may be introduced on one construct or separate constructs, including any combination of two of said genes on a single first construct in combination with a second construct comprising one of said genes which is not comprised in said first construct. Constructs as described above may be hosted in an organism which then subsequently may be used for said cloning in a host system as mentioned above.

According to a particular embodiment, the present invention provides a method for in vivo synthesis of holo-photoactive yellow protein comprising the steps of: (a) providing a first construct, said first construct comprising a dual biosynthetic gene operon consisting essentially of a tyrosine ammonia lyase gene and a p-hydroxycinnamyl:CoA ligase gene, wherein said genes are operably linked to a suitable regulatory sequence; (b) providing a second construct, said second construct comprising a further biosynthetic gene, said further biosynthetic gene being a photoactive yellow protein, wherein said photoactive yellow protein is operably linked to a suitable regulatory sequence; (c) introducing said first and second constructs into a host expression system; (d) culturing said host expression system under conditions allowing expression of said biosynthetic genes; and (e) recovering holo-photoactive yellow protein.

In one embodiment, the present invention provides a method for (in vivo) synthesis of holo-photoactive yellow protein wherein said tyrosine ammonia lyase and optionally said p-hydroxycinnamyl:CoA ligase genes are bacterial genes.

In a further embodiment, the present invention provides a method wherein said tyrosine ammonia lyase and optionally said p-hydroxycinnamyl:CoA ligase genes are derived from Rhodobacter.

In yet a further embodiment, a method is provided wherein said tyrosine ammonia lyase and optionally said p-hydroxycinnamyl:CoA ligase genes are derived from *Rhodobacter capsulatus*.

In yet a further embodiment, the present invention provides a method wherein said host expression system is chosen from the group comprising bacteria, yeasts, filamentous fungi, algae, and plant cells.

In yet a further embodiment, the present invention provides a method wherein said host expression system is a bacterial cell.

In yet a further embodiment, the present invention provides a method wherein said bacterial cell is *Escherichia coli*.

In yet a further embodiment, the present invention provides a method wherein said suitable regulatory sequence is an inducible promoter sequence.

Accordingly, in yet a further embodiment, the present invention provides a method wherein said inducible promoter may be an inducible tac promoter.

The present invention further provides a product obtainable by any of the previous methods.

The present invention further provides a product obtainable by a method as described herein, for use as photochromic substance in production of electro optical random access memory.

The present invention further provides a product obtainable by a method as described herein, for use as photochromic substance in production of liquid crystal polymers (with applications such as for LCD technology).

The present invention further provides a product obtainable by a method as described herein for use as photochromic substance in biochips The present invention further provides a product obtainable by a method as described herein for use as photochromic substance in light-inducible gene expression systems.

The present invention further provides an isolated nucleic acid sequence encoding a biosynthetic protein, said biosynthetic protein comprising a TAL or tyrosine ammonia lyase activity, or encoding an immunologically active and/or functional fragment of said protein, said isolated nucleic acid comprising or consisting of at least a functional part of the nucleic acid sequence as given in SEQ ID NO: 3, or the complement thereof.

In one embodiment of the present invention, said TAL encoding nucleic acid sequence may be DNA, cDNA, genomic DNA or RNA wherein T is replaced by U.

The present invention further provides a TAL encoding nucleic acid sequence encoding a protein as defined in SEQ ID NO: 4.

The present invention further provides a vector comprising a nucleic acid sequence encoding TAL as described herein.

In one embodiment of the present invention, said vector may be an expression vector wherein the nucleic acid sequence encoding TAL is operably linked to at least one control sequence allowing the expression of said sequence in prokaryotic and/or eukaryotic host cells.

The present invention further provides a host cell comprising a nucleic acid molecule encoding TAL or a vector comprising said TAL encoding sequence as described herein.

In one embodiment of the present invention, said host cell may be a bacterial, insect, fungal, plant, or animal cell.

In a further embodiment of the present invention, a nucleic acid sequence encoding TAL is integrated into the genome of said host cell.

The present invention further provides an isolated polypeptide encodable or encoded by a nucleic acid sequence encoding TAL as described herein, or a homologue or a derivative thereof, or an immunologically active and/or functional fragment thereof.

In one embodiment of the present invention, said polypeptide has an amino acid sequence as given in SEQ ID NO: 4, or a homologue or a derivative thereof, or an immunologically active and/or functional fragment thereof.

In another embodiment of the present invention, a nucleic acid sequence encoding TAL is provided as described herein for synthesis of para-hydroxycinnamic acid.

The present invention further provides a method for synthesis of para-hydroxycinnamic acid comprising the use of a TAL polypeptide as described herein.

The present invention further provides an antibody specifically recognizing a TAL polypeptide as described herein.

The present invention further provides a composition comprising at least a TAL nucleic acid, a vector, a polypeptide, or an antibody, as described herein.

According to the present invention, a TAL enzyme is provided which is capable of producing para-hydroxycinnamic acid from L-tyrosine and which converts L-phenylalanine to cinnamic acid, albeit with a much lower catalytic efficiency. Thus, the present invention further provides a method for synthesis of para-hydroxycinnamic acid, which comprises introducing a nucleic acid sequence encoding TAL as described above under control of suitable regulatory regions in a host expression system, culturing said host expression system under conditions allowing the expression of said TAL and, optionally, recovering said para-hydroxycinnamic acid.

"sequence identity" of two sequences as used herein relates to the number of positions with identical nucleotides or amino acids divided by the number of nucleotides or amino acids in the shorter of the sequences, when the two sequences are aligned. Preferably said sequence identity is higher than 70%-80%, preferably 81-85%, more preferably 86-90%, especially preferably 91-95%, most preferably 96-100%, more specifically is 100%.

A "fragment" of a DNA molecule or protein sequence as used herein refers to a truncated sequence of the original (nucleic acid or amino acid) sequence referred to, which can vary in length but of which the minimum size is sufficient to ensure the (encoded) protein to be biologically active, the maximum size not being critical.

Unless stated otherwise in the Examples, all recombinant DNA techniques are carried out according to standard protocols as described in Sambrook and Russell (2001) Molecular Cloning: A Laboratory Manual, Third Edition, Cold Spring Harbor Laboratory Press, NY, in Volumes 1 and 2 of Ausubel et al. (1994) Current Protocols in Molecular Biology, Current Protocols, USA and in Volumes I and II of Brown (1998) Molecular Biology LabFax, Second Edition, Academic Press (UK). Standard materials and methods for polymerase chain reactions can be found in Dieffenbach and Dveksler (1995) PCR Primer: A Laboratory Manual, Cold Spring Harbor Laboratory Press, and in McPherson at al. (2000) PCR—Basics: From Background to Bench, First Edition, Springer Verlag, Germany.

SHORT DESCRIPTION OF THE DRAWINGS

The above detailed description, given by way of example, but not intended to limit the invention to specific embodiments described, may be understood in conjunction with the accompanying Figures, incorporated herein by reference, in which:

FIG. 1 is a chemical reaction sequence showing the biosynthesis of holo-photoactive yellow protein (PYP). Tyrosine ammonia lyase (TAL) catalyses the conversion of L-tyrosine to p-hydroxycinnamic acid. Subsequently, the chromophore is presumably activated by binding to CoA at the expense of ATP. This is catalysed by a p-hydroxycinnamyl:CoA ligase (pCL). The activated chromophore is presumably chemically attached to the apo-protein without the use of any additional enzymes.

FIG. 2 is a presentation of the pH optima for PAL/TAL activity. The solid line is a theoretical curve for the pH dependence of the rate of TAL reaction. The dotted line is for the PAL reaction.

FIG. 3 shows Lineweaver-Burk plots of the TAL (A) and PAL (B) activities of the *Rhodobacter. capsulatus* enzyme.

FIG. 4 shows high pressure liquid chromatograms for PAL and TAL assays, showing the reaction mixture compounds at zero time (A and C, peaks 1 and 3 are L-Phe and L-Tyr resp.) and the formation of cinnamic acid (B, peak 2) and p-hydroxycinnamic acid (D, peak 4) after 20 min of incubation. Thin lines are absorbances at 220 nm in A and B, and at 280 nm in C and D. Thick lines are at 280 nm in A and B, and at 310 nm in C and D.

FIG. 5 is a presentation of the expression vectors used in the dual plasmid system.

Figure 6:
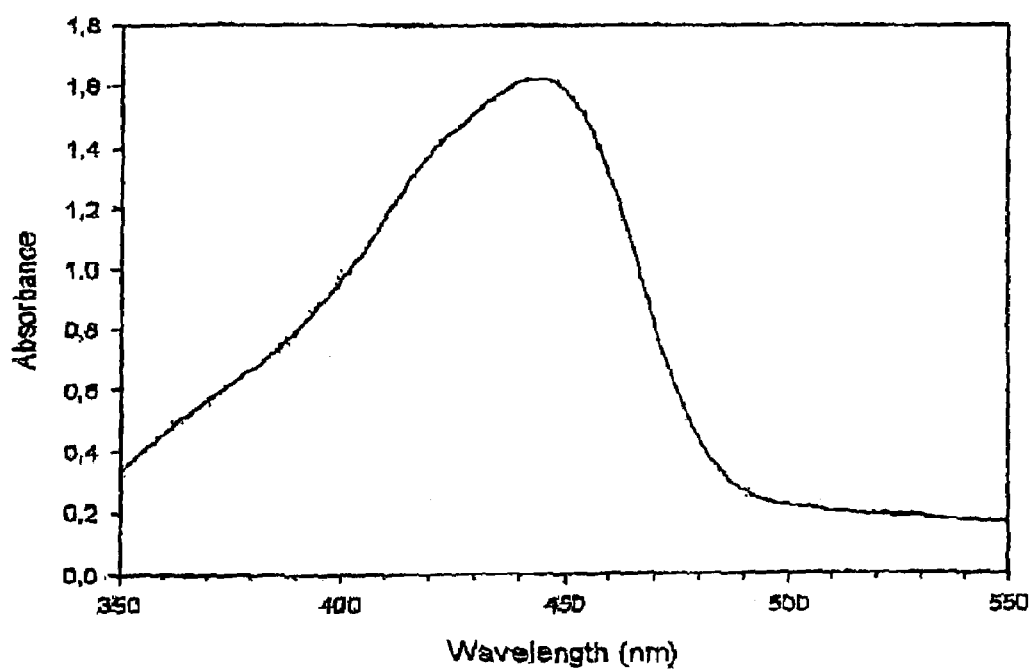

FIG. 6 shows a crude holo-PYP absorption spectrum. Cells were induced for 16 h and broken by sonication. Crude cell lysate from cells containing only the pET20b(pyp) served as a blank.

FIG. 7 is a SDS-PAGE pattern.

Figure 7A:
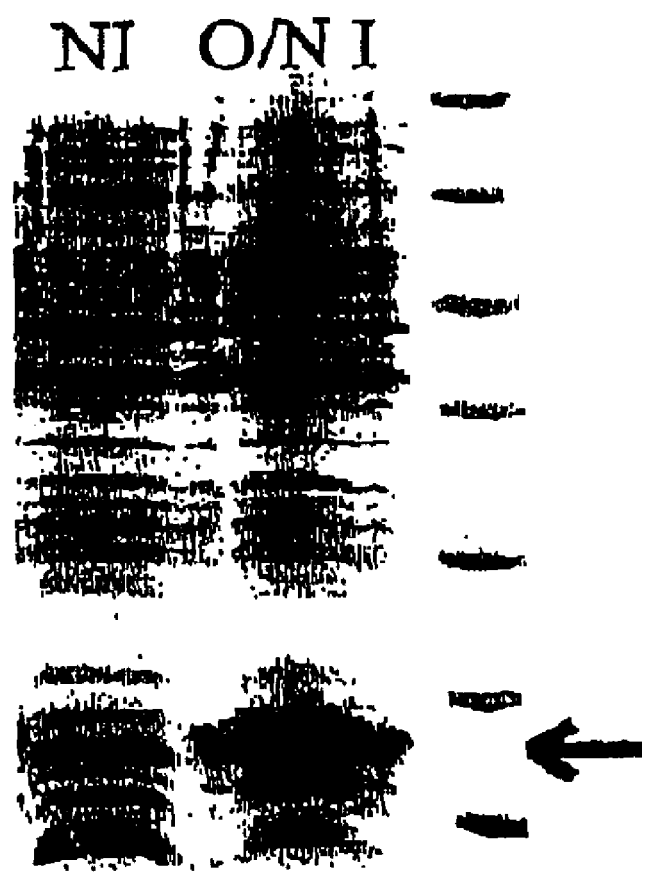

FIG. 7a shows a SDS-PAGE pattern of a crude cell extract before (NI) and after (O/N I) overnight induction. The proteins were visualised by Coomassie staining. The arrow indicates the 14 kDa PYP.

Figure 7B:
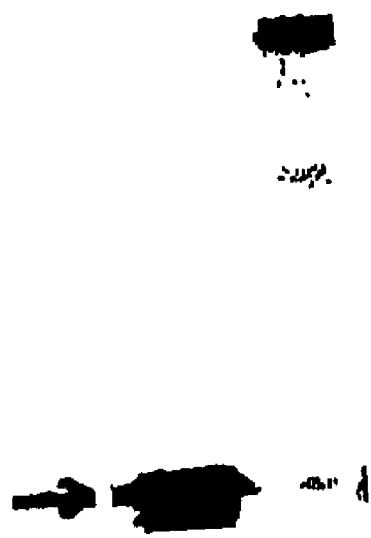

FIG. 7b shows a silver stained SDS-PAGE gel of the purified holo-PYP.

Figure 8:
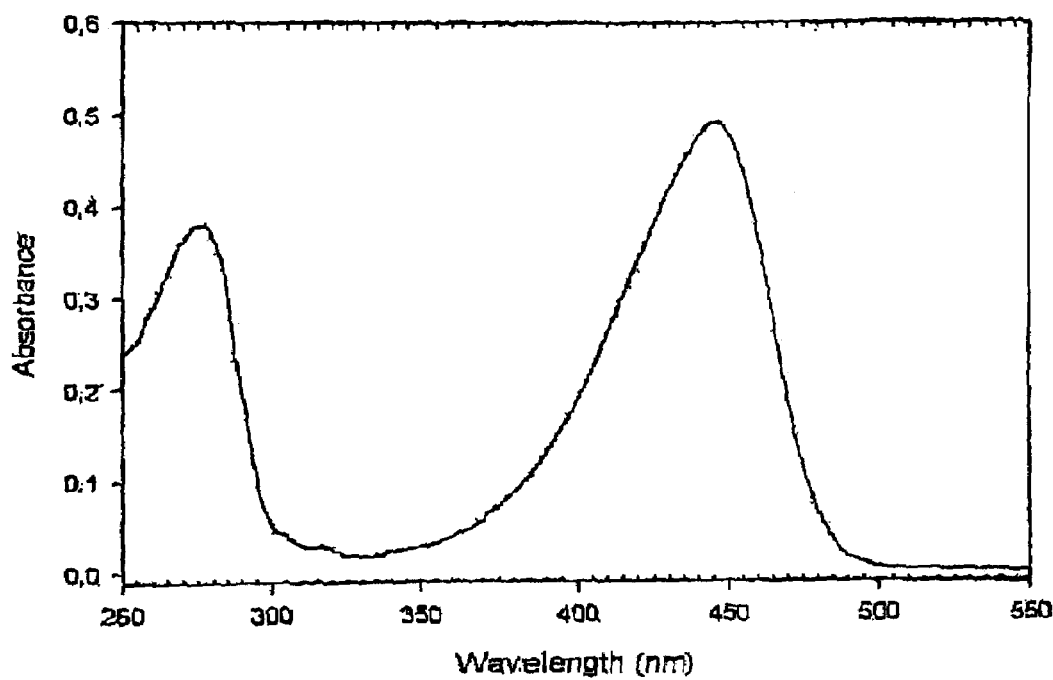

FIG. 8 is an absorption spectrum of the purified holo-PYP in Tris-HCl buffer at pH 9.0. No apo-protein could be detected by mass spectrometry.

FIG. 9 shows the kinetics of the light-induced absorbance changes: I1→I2 bleaching reaction (A) and I2→P recovery (B). The excitation wavelength was 440 nm. The sample contained PYP with an absorption of 0.2 at 446 nm. Measurements were performed at pH 8.0 in universal buffer.

In the description and examples, reference is made to the following sequences:

| | |
|---|---|
| SEQ ID No 1: | nucleotide sequence encoding a PYP from *Halorhodospira halophila* |
| SEQ ID No 2: | amino acid sequence of a PYP polypeptide from *Halorhodospira halophila* |
| SEQ ID No 3: | nucleotide sequence encoding a TAL from *Rhodobacter capsulatus* |
| SEQ ID No 4: | amino acid sequence of a TAL polypeptide from *Rhodobacter capsulatus* |
| SEQ ID No 5: | nucleotide sequence encoding a pCL from *Rhodobacter capsulatus* |
| SEQ ID No 6: | amino acid sequence of a TAL polypeptide from *Rhodobacter capsulatus* |
| SEQ ID No 7: | primer ECOTAL |
| SEQ ID No 8: | primer TALHIND |
| SEQ ID No 9: | primer sphlpKK |
| SEQ ID No 10: | primer TALHindIII |
| SEQ ID No 11: | primer ECOpCL |
| SEQ ID No 12: | primer pCLHIND |
| SEQ ID No 13: | primer HindHYBpCL |

EXAMPLES

Experiments have been conducted which include the cloning of the PYP biosynthetic pathway and the production of holo-PYP in *Escherichia coli* to a high internal concentration. *Rhodobacter capsulatus* (DSMZ 1710, type strain) was obtained from the 'Deutsche Sammlung von Mikroorganismen und Zellkulturen GmbH (DSMZ). *Escherichia coli* BL21 (DE3) was obtained from Novagen (Madison, Wis., USA). Luria Broth (LB) and antibiotics were prepared according to the methods described in Sambrook et al. (1989). The pACYC184 vector was obtained from NEBiolabs (Beverly, USA). The pET15b vector was obtained from Novagen (Madison, Wis., USA) and the pKK223-3 vector was obtained from Pharmacia (Uppsala, Sweden).

Example 1

Cloning and Purification of the tal Gene from *Rhodobacter capsulatus*

Cloning of the tal gene of *Rhodobacter capsulatus* (DSMZ 1710, type strain) in the overexpression vector pKK223-3 was performed using PCR (polymerase chain reaction)-based techniques. The oligonucleotides ECOTAL (CGGAATTCATGCTCGATGCAACC—SEQ ID NO: 7) and TALHIND (GCCCAAGCTTTCATGCCGGGG-GATC—SEQ ID NO: 8) were complementary to the DNA encoding the TAL N- and C-termini. ECOTAL and TAL-HIND contained an EcoRI and a HindIII restriction site, respectively. As template for the PCR we used *Rhodobacter capsulatus* genomic DNA, prepared according to Sambrook et al. (1989). The amplified 1.6 kb fragment was digested with EcoRI and HindIII and inserted into the predigested pKK223-3 plasmid.

After DNA sequencing, it was found that there were four differences in the gene sequence, resulting in two differences in the translated polypeptide sequence, as compared to what was found in the on-going genome sequence project. Both differences were found in non-conserved regions, namely the mutation His522→Asp and the deletion of Ala535. The PCR and sequencing reactions were repeated three times, and always gave the same results. We attribute these differences to either strain differences or genome sequencing errors.

pKK223-3(TAL), with expression of the tal gene under control of a strong tac promotor, was transformed into *Escherichia coli* XL1-Blue competent cells. The overexpression culture, induced with 1 mM IPTG (isopropyl-β-D-1-thiogalactoside) at an optical density measured at 600 nm ($OD_{600}$) of 0.5, was grown overnight at 37° C. Expression samples were taken after several induction times and analysed by SDS-PAGE. After 2 h of induction, recombinant protein could already be detected, but maximum production was achieved after overnight induction. The cells were pelleted by centrifugation, resuspended in Tris-HCl buffer (20 mM, pH 8.0), and fractionated by sonication. After centrifugation to remove the cell debris, the TAL protein was precipitated by ammonium sulfate at a saturation of 25-40%. Following dialysis, the TAL-containing fraction was loaded onto a 1 ml Resource Q column (Pharmacia, Uppsala, Sweden) using an ÄKTA Explorer (Pharmacia) HPLC system. Buffer A contained 20 mM TRIS-HCl, pH 8.0; buffer B was the same as A, supplemented with NaCl to a final concentration of 1M. The TAL-containing fractions were pooled and concentrated on centrifugal filters Ultrafree 4 (Millipore, Bedford, Mass.). The purification was continued by size exclusion chromatography on a Superdex 75 column (Hiload 16/60, Pharmacia) with 100 mM Tris-HCl pH 8.0, supplemented with 150 mM NaCl. After this step, the TAL was approximately 90% pure. An additional anion exchange 'polishing' step (Resource Q) removed practically all remaining contaminating proteins. We were able to reach a purity of 99%, based on a silver stain procedure. The final yield of the recombinant protein after purification was at least 5 mg/L culture.

Example 2

Enzymatic Characterization of TAL

The purified protein was investigated with respect to its enzymatic activity and specificity by determining the $K_M$ and $k_{cat}$ values for the conversion of L-tyrosine to p-hydroxycinnamic acid and L-phenylalanine to cinnamic acid. Both activities were followed by the following spectrophotometric assay (adapted from Rösler et al. (1997)): PAL activity was assayed by following cinnamic acid formation at 280 nm using a double beam spectrophotometer (Uvikon, Kontron, Herts, United Kingdom) in 10 mM Tris buffer at 35° C. The pH optimum was determined between the pH values 6-10. The substrate concentrations were varied between 5 mM and 0.2 mM. TAL activity was assayed by monitoring p-hydroxycinnamic acid formation at 310 nm and 35° C. The substrate concentration was varied between 2 mM and 0.01 mM. All reactions were performed in a total volume of 1 ml.

Figure 1:
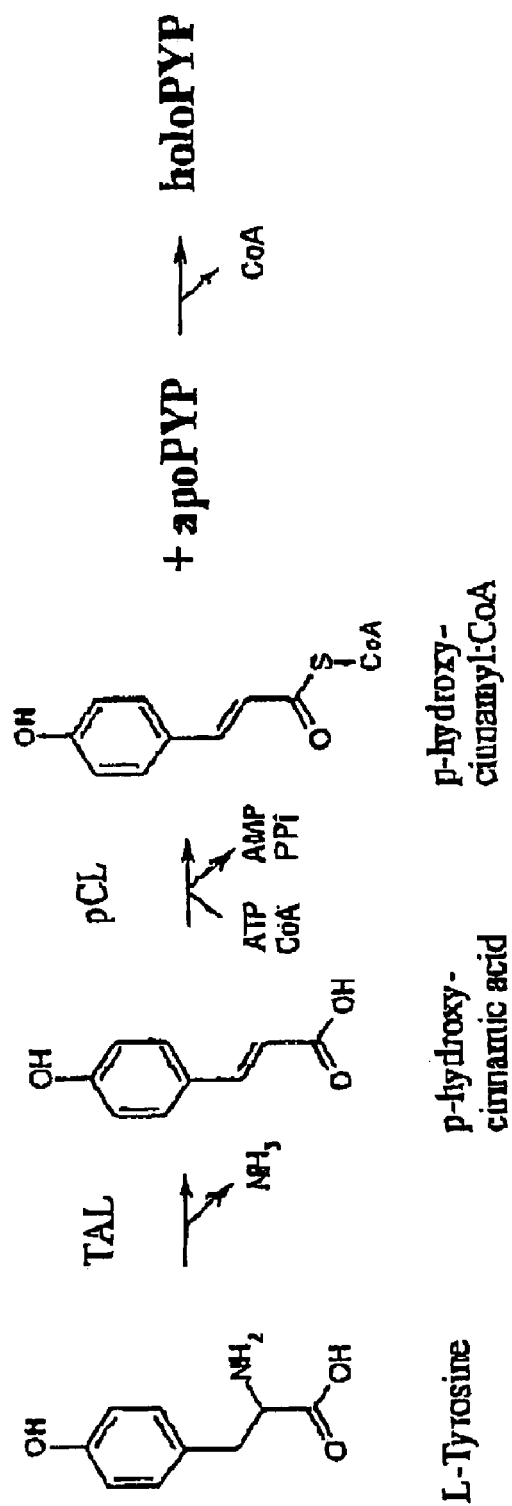
Figure 2:
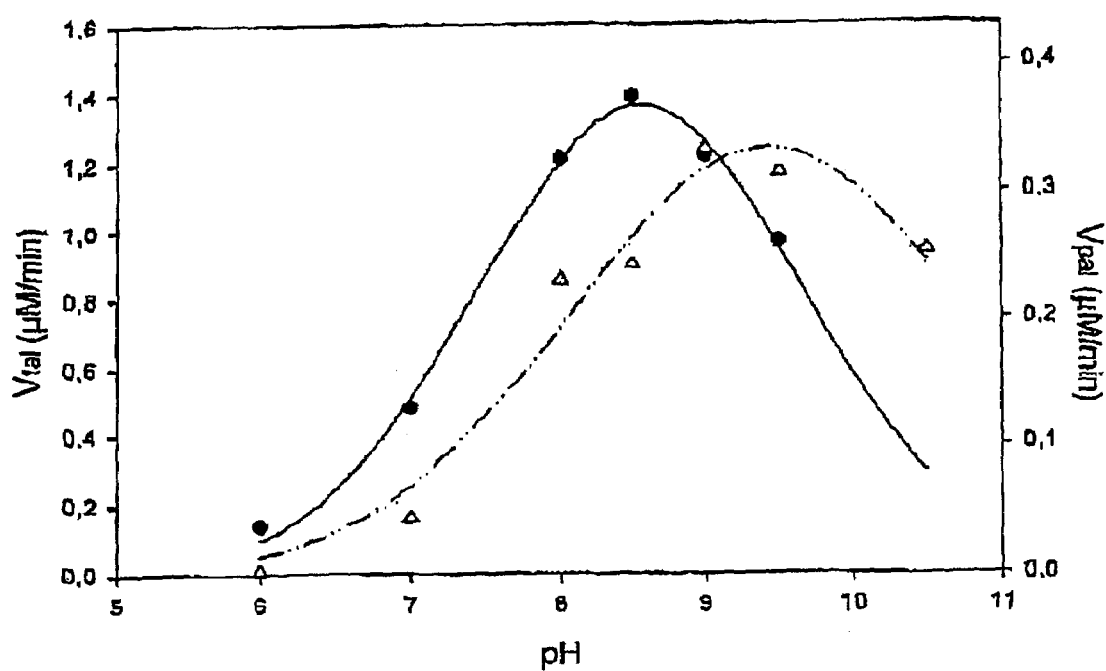
Figure 3:
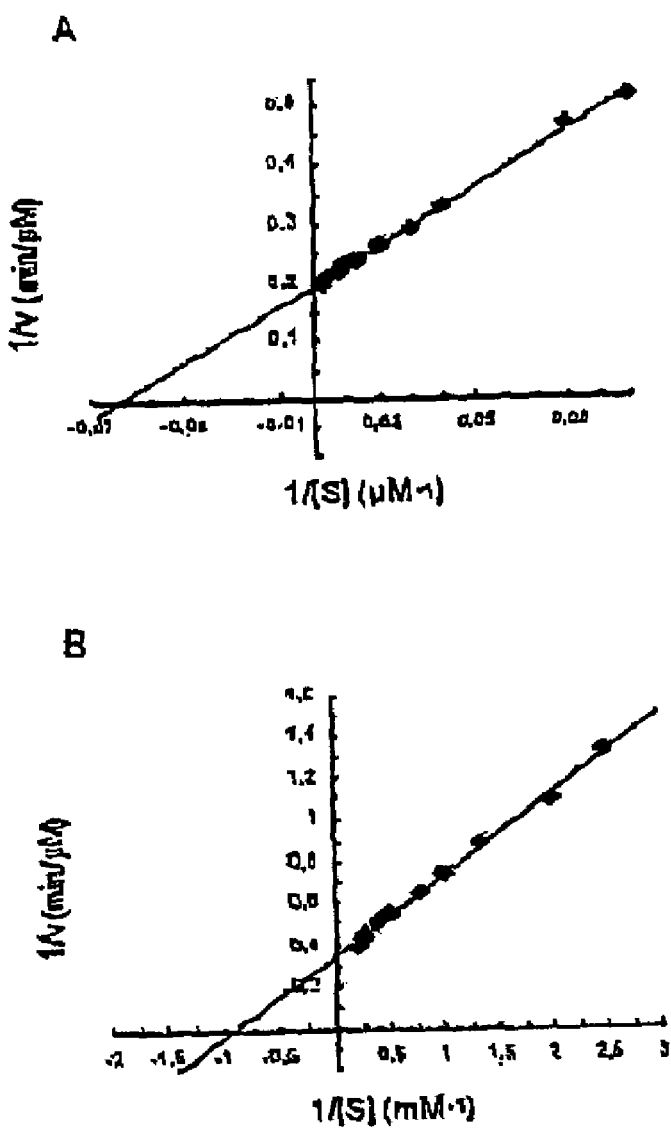

The pH optima of both activities were found to be slightly different as shown in FIG. 2; the optimum was pH 8.5 for TAL and pH 9.4 for PAL. FIG. 3 presents Lineweaver-Burk plots for the two substrates at their respective pH optimum. The kinetic parameters calculated for TAL and PAL activities are summarized in Table 1. As a consequence of a smaller Km and a slightly larger $k_{cat}$, we can conclude that the enzyme shows a strong preference for L-tyrosine over L-phenylalanine. For comparison, Table 1 also includes the kinetic parameters for the PAL/TAL enzyme from the monocot *Zea mays*, for both substrates at pH 8.7 (Rösler et al., 1997). It can be seen that there is a 15-fold higher Km value for L-Phe compared to L-Tyr. With the Rhodobacter capsulatus enzyme, we found an even more pronounced specificity for L-Tyr, with an 80-fold higher Km for L-Phe than for L-Tyr. In maize, the turnover numbers (kcat) for TAL activity are about one tenth those for the PAL activity, resulting in a comparable catalytic efficiency ($k_{cat}$/Km). In *Rhodobacter capsulatus*, on the other hand, the $k_{cat}$ for TAL activity is almost two times higher than for PAL activity. This results in a 150-fold greater catalytic efficiency for L-Tyr than for L-Phe.

Table 1 also shows that the Km value and turnover number of the *Rhodobacter capsulatus* enzyme, with L-tyrosine as substrate, are very comparable to the kinetic parameters from the PAL-1 isozyme from parsley (*Petroselinum crispum*), with L-phenylalanine as substrate, the latter is a typical PAL from dicots (Appert et al., 1994).

Since PAL and TAL sequences show significant homology to histidine ammonia lyases (HAL), which are common enzymes in bacteria, we also tested L-histidine as a substrate for the recombinant enzyme. However, using the spectrophotometric assay described by Schwede et al. (1999), we could not detect any activity. Also L-tryptophan is not a substrate, since no activity was detected even up to a 5 mM concentration.

Example 3

Identification of the Products Formed by the TAL Enzyme

Figure 4:
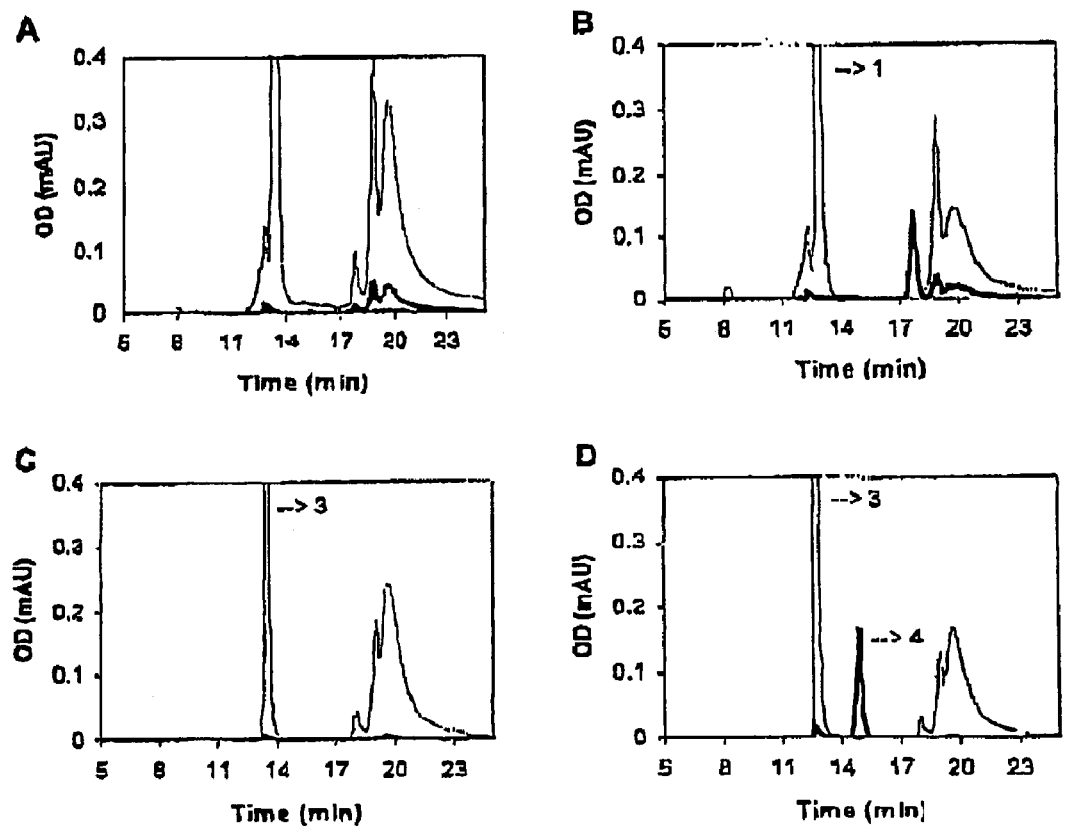

For the determination of PAL and TAL specifications, 1 mM L-Phe or 1 mM L-Tyr was used. The reaction was left at 25° C. for 20 min in TRIS-HCl buffer (10 mM, pH 8.0) and followed spectrophotometrically. The reaction was stopped by adding 30 µl 2N HCl. After filtration on a 0.45 µM Millipore filter, samples were analysed on a C18 column (220×2.1 mm, Applied Biosystems, Foster City, Calif.) connected to the SMART HPLC system (Pharmacia). Solvent A consisted of 0.1% TFA (trifluoroacetic acid), and solvent B of 0.08% TFA containing 80% acetonitrile. The flow rate was 100 µl/min. Peaks were detected by their characteristic UV absorbance. As shown in FIG. 4, the products had retention times as expected for cinnamic acid and p-hydroxycinnamic acid, which is in agreement with PAL and TAL activities.

Our findings clearly show that the pal-homologous gene, which was found in *Rhodobacter capsulatus*, codes for a tyrosine ammonia lyase. The catalytic efficiency for L-phenylalanine is 150 times less than that for L-tyrosine as the substrate, suggesting that the principal physiological role of this enzyme is the production of p-hydroxycinnamic acid. To our knowledge, this is the first enzyme of the PAL/TAL family that has a higher, even substantially higher, enzymatic efficiency with L-tyrosine than with L-phenylalanine. In addition, it is also the first bacterial tyrosine ammonia lyase that has been identified. The most commonly encountered enzyme of this family in bacteria is HAL, but our enzyme had no activity with histidine at all.

Example 4

Construction of a Dual Biosynthetic Gene Operon Containing the Two Biosynthetic Genes, and Recloning of the pyp Gene In order to produce the dual biosynthetic gene operon, we first recloned the tal gene into pACYC184 (NEBiolabs, Beverly, USA). Since the plasmid does not contain an inducible promotor or a multicloning site, we PCR-amplified a 200 bp region which included the tac promotor together with the tal gene. As template, we used our pKK223-3(TAL) plasmid that was constructed earlier (Kyndt et al, 2002). The primers used for this amplification were SphIpKK (ACAT<u>GCATGC</u>GGAAGCTGTGGTATG GCTG—SEQ ID NO: 9) and TALHindIII (GCCC<u>AAGCTT</u> TCATGCCGGGGGATC—SEQ ID NO: 10) (restriction sites are underlined). We cloned the amplified 1826 bp fragment into the pACYC184 vector as a SphI-HindIII fragment. This disrupted the tetracycline resistance gene of the vector, and resulted in the pACYC(TAL) plasmid (not shown).

Figure 5A:
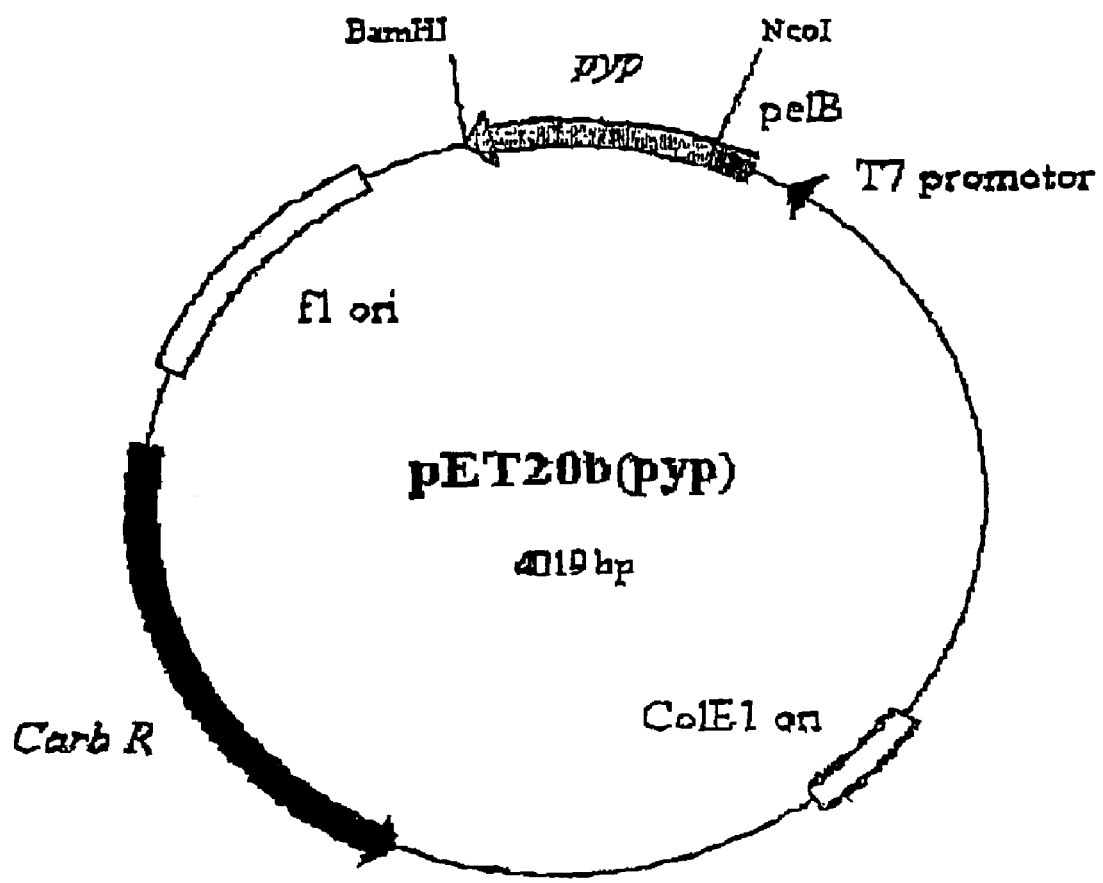
FIG. 5a shows pET20b(pyp), which was constructed as described by Genick et al. (1997), and has a carbinicillin resistance gene (carb resist). In front of the pyp gene, there is a pelB leader.

The pcl gene was cloned into the pKK223-3 vector (Pharmacia) in an analogous way as we described earlier for the tal (Kyndt et al., 2002). Genomic DNA from *Rhodobacter capsulatus* was prepared according to Sambrook et al. (1989), and served as a template in the PCR reaction. The following primers were used to amplify the gene coding for pCL: ECOpCL (CG<u>GAATTC</u>ATGAACTCGACGAT GCC—SEQ ID NO: 11) and pCLHIND (CGC<u>AAGCTT</u>CA GTCCCMTCCCG—SEQ ID NO: 12). The amplified pcl fragment was digested with EcoRI and HindIII and ligated into the pre-digested pKK223-3. With the resulting pKK (pCL) construct as template, PCR was used to amplify a 1311 bp fragment with the following primers: HindHYB-pCL (TCCC<u>AAGCTT</u>GTGGAATTGTGAGCGGATA AC—SEQ ID NO: 13) and pCLHind (CGC<u>AAGCTT</u>CAGT CCCAATCCCG—SEQ ID NO: 14). These primers were designed in such a way that the amplified fragment contained the ribosome binding site of the pKK223-3 vector, followed by the gene for pCL. This fragment was cloned after the tal gene as a HindIII-HindIII fragment in the pACYC(TAL). This yields the expression plasmid pACYC (TALpCL), which has both tal and pcl under the control of an inducible tac promotor (see FIG. 5*c*), and contains a p15A origin of replication and a chloramphenicol resistance encoding gene. The orientation of the pcl fragment was checked with restriction digest analysis and sequencing. The construction of a synthetic operon containing tal and pcl allowed us to express both genes by inducing the strong tac promotor with IPTG.

Figure 5B:
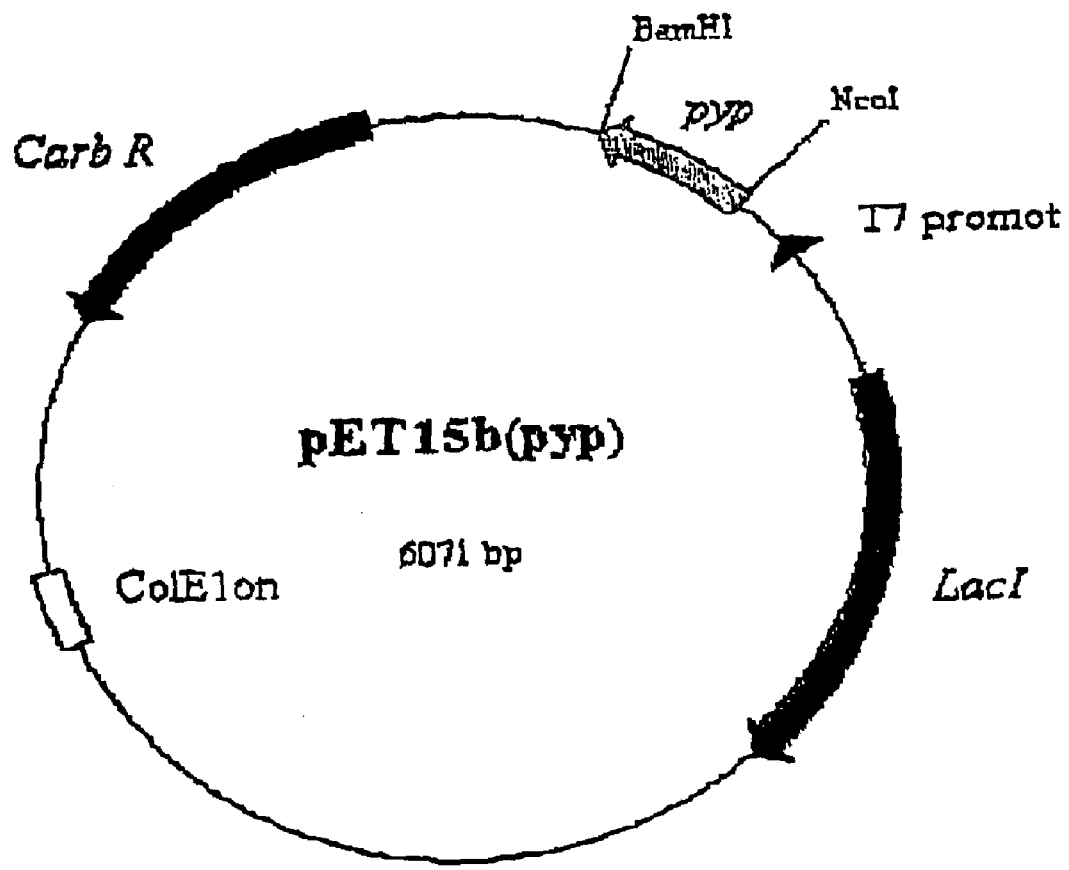
FIG. 5b shows the pET15b(pyp), which also has a carbenicillin resistance gene.
Figure 5C:
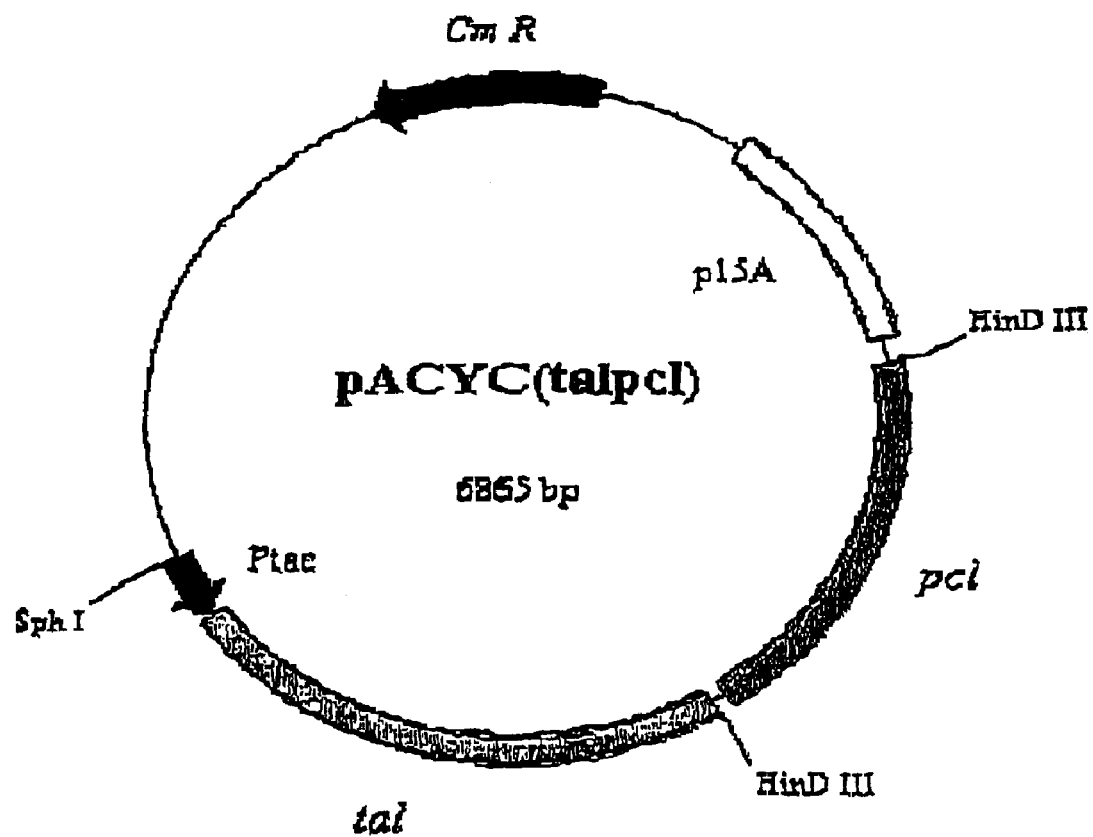
FIG. 5c shows the pACYC(talpcl), on which a chloramphenicol resistance gene is encoded (Cm resist). Both tal and pcl are under the control of an inducible tac promotor.

The cloning of the pyp gene from *Halorhodospira halophila* has been described elsewhere (Genick et al., 1997). There, the gene was cloned into the pET20b vector (Novagen, Madison, Wis., USA), where it was preceded by a pelB leader sequence. This pET20b(PYP) construct was provided to us by professor T. E. Meyer (University of Arizona, Tucson, Ariz., USA). To achieve cytoplasmic production of the PYP, we recloned the gene into pET15b (Novagen). This was done by digesting the pET20b(PYP) with NcoI and BamHI restriction enzymes, which gave us the 375 bp pyp fragment (without the pelB leader sequence). This was ligated into pre-digested pET15b, resulting in pET15b(PYP) (FIG. 5*b*). By cloning the pyp in this manner, the His-tag encoding sequence was removed from the pET15b.

Since the pACYC(TALpCL) construct has a different origin of replication and antibiotic resistance-encoding genes from pET20b(PYP) (see FIG. 5a, and Genick et al, 1997), it is possible to maintain both plasmids in the same cell by continuous selection with carbenicillin and chloramphenicol.

Example 5

Production of TAL, pCL and PYP in *Escherichia coli* BL21(DE3) and Purification of Holo-PYP

*Escherichia coli* BL21 (DE3) cells were made competent and subsequently transformed with the pACYC(TALpCL) construct by electroporation. In turn, clones containing the plasmid considered were made competent and transformed with the pET20b(PYP) construct. A culture containing the genes for TAL, pCL and apo-PYP, was grown on carbenicillin and chloramphenicol antibiotics. Growth was carried out at 28° C. until an optical density (OD) (measured at 600 nm) of 0.6, and induced with a final concentration of 0.5 mM IPTG.

After 4 h of induction, the cultures were centrifuged; the pellet already displayed a bright yellow color. The amount of yellow color increased with longer induction times, with an estimated maximum after 16 h of induction. Cells containing neither of the plasmids, and cells harbouring only pET20b (PYP) or only pACYC(TALpCL) served as controls: centrifugation of these cultures after induction did not result in a yellow-coloured pellet. Since the pCL enzyme has not been enzymatically characterised, it was important to determine if pCL was necessary for holo-PYP synthesis. To this end, constructs were grown with TAL as the only biosynthetic enzyme. This was done by transforming pET20b (PYP)-bearing cells with the pACYC(TAL) plasmid. After 4 h of induction, these co-transformants did not show any color change. This unambiguously shows that pCL is necessary for the in vivo formation of holo-PYP.

The yellow colored cells that contained the genes for TAL, pCL and PYP were resuspended in TRIS-HCl buffer (50 mM, pH 9.0) and freeze-thawed two times, after which they were further fractionated by sonication and centrifugation to remove the cell debris. These crude cell extracts were analysed spectrophotometrically in the 350-550 nm region. Extracts of cells with only the pET20b(PYP) construct served as a blank. It can clearly be seen from the spectrum in FIG. 6 that there is an absorbance peak with a maximum around 445 nm, which is consistent with the wild-type *Halorhodospira halophila* PYP. This is a first indication that the PYP has been reconstituted in vivo and has the expected conformation of the ground state. The maximum amount of holo-PYP present in these crude cell extracts was calculated to be around 60-80 mg of holo-protein per liter of culture. We found that non-induced overnight cultures, containing all three considered genes, also produced holo-PYP with a yield of approx. 15 mg of holo-PYP in crude cell extracts per liter of culture.

FIG. 7a shows an SDS-PAGE of whole cells containing both plasmids, before and after overnight induction. The production of PYP can clearly be seen at 14 kDa. Although the above experiments showed that TAL and pCL production was necessary for holo-PYP production, we were unable to unambiguously show the expression of either tal or pcl on SDS-PAGE gels of different concentrations. This is likely to be a consequence of the low copy number of the pACYC vector, but even a limited amount of the biosynthetic enzymes is sufficient to produce large amounts of activated chromophore. In order to determine if the PYP from the two-plasmid construct undergoes a normal photocycle and displays normal kinetics, we purified the yellow protein. This was done by applying the crude cell extract to a 10 ml Q-Sepharose FF column (Pharmacia Uppsala, Sweden), a TRIS-HCl buffer (50 mM, pH 9.0) was used to apply the sample, and proteins were eluted with the same buffer supplemented with an increasing amount of NaCl. The PYP eluted at approximately 250 mM NaCl. The yellow-coloured fractions were pooled and concentrated on Ultrafree-4 centifugal filters (Millipore, Bedford, Mass.). The purification was continued by size exclusion chromatography on a Superdex 75 column (Hiload 16/60, Pharmacia) with 100 mM TRIS-HCl, pH 8.0, supplemented with 50 mM NaCl as running buffer. This was performed using an AKTA Explorer HPLC system (Pharmacia). After dialysing the yellow sample, we proceeded with the purification on a MonoQ (HR 5/5, Pharmacia) anion exchange column. The purified PYP was found to have a purity of about 98%, based on silverstaining of an SDS-PAGE gel (FIG. 7b). As can be seen from FIG. 8, the protein still has the characteristic 445 nm absorption. The yield of purified holo-PYP was approximately 40 mg of holo-protein per liter of culture, which is more than twice as high as the yield found by Genick et al. (1997), where the chromophore was chemically attached to the recombinant apo-PYP. The ratio of the 445 nm to the 280 nm absorption is approximately 2.2 for 98% purified protein. This is identical to the best ratios found for highly purified PYP from *Halorhodospira halophila*.

Example 6

Analysis of the Recombinant Holo-PYP by Mass Spectrometry

To ascertain that the in vivo formed PYP has covalently attached p-hydroxycinnamic acid, we analysed the purified protein by mass spectrometry (MS). The mass was determined in the denatured state of the protein by the use of an electrospray Q-TOF mass spectrometer equipped with a nano-electrospray source. Approximately 5-10 pmol of protein was dissolved in 5 µl 50% acetonitrile/0.1% formic acid and loaded into a nanospray capillary. The observed mass was 14020 Da, which is 147 Da larger than the theoretically calculated mass of the apo-protein, corresponding to the mass of chromophore plus protein. This result is in agreement with the MS results for wild type PYP reported by Van Beeumen et al. (1993). When the PYP sample was analysed by mass spectroscopy after the size exclusion purification step, there was evidence of a small amount of non-reconstituted apo-PYP. After further fractionation with the MonoQ column as described above, apo-PYP could not be detected by mass spectrometric analysis. This, together with the 445 nm to 280 nm absorption ratio of 2.2, indicates that the holo-PYP was fully separated from the apo-form during the last purification step. After digesting the holo-PYP with trypsin, we performed MS/MS measurements, which confirmed that the p-hydroxycinnamic acid is attached to Cys 69, as was found with wild-type PYP.

Example 7

Comparison of Periplasmic Versus Cytoplasmic Expression of PYP

In order to investigate whether the occurrence of apo-PYP is related to the periplasmic production of the protein, we recloned the pyp gene into the pET15b vector that did not contain the pelB leader sequence. By expressing the gene from this construct we could achieve a cytoplasmic production of PYP. Transformants containing both pET15b(PYP) and the pACYC(TALpCL) were tested for their ability to produce holo-PYP, in a way analogous to what we described for the pET20b(PYP) construct. The yield of holo-PYP in crude cell extracts was approximately the same as with the periplasmic PYP production, and there was still evidence of apo-PYP in the partially purified protein sample. This could be a consequence of the misfolding of some of the apo-PYP, since chemical reconstitution from purified apo-PYP leads to very low yields (unpublished result). However, an induction of the biosynthetic genes prior to the pyp gene may yield a higher ratio of holo- to apo-PYP, or expression of the biosynthetic genes on a high copy number plasmid would increase the amount of the biosynthetic enzymes and therefore of holo-PYP.

Example 8

Figure 9A:
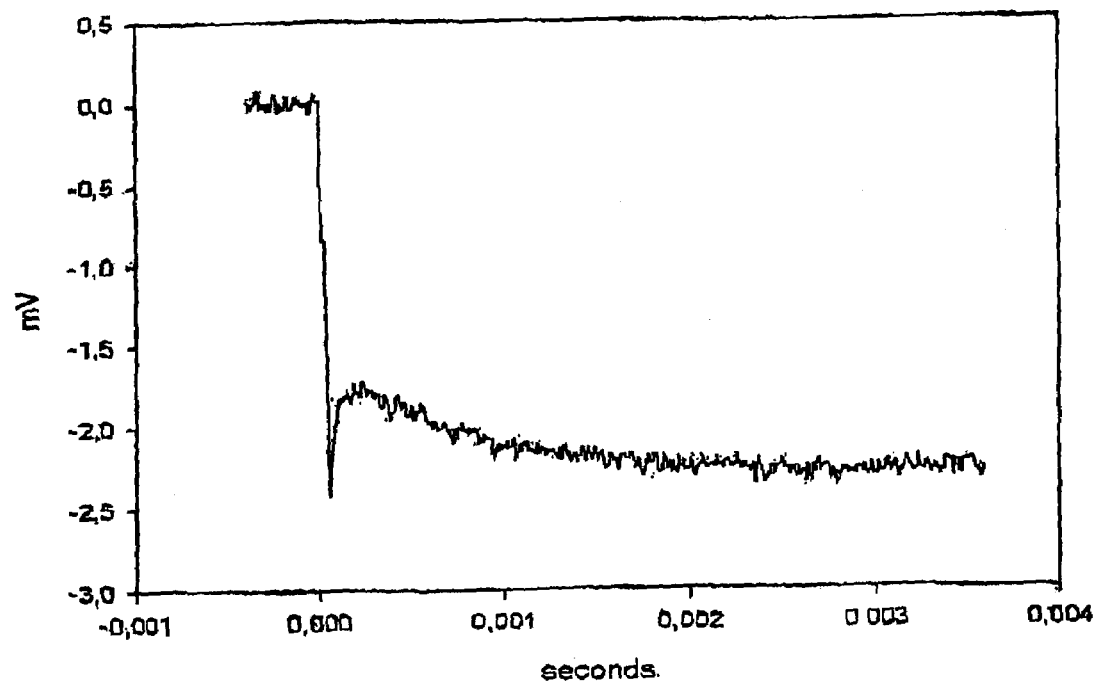
Figure 9B:
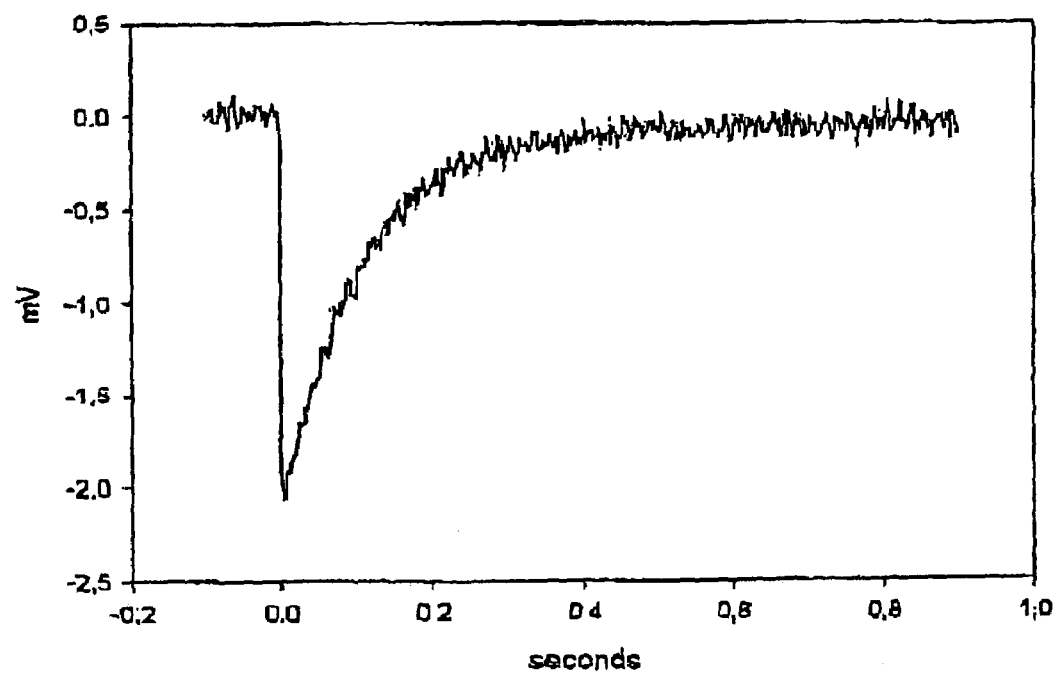

Comparison of the Photocycle Kinetics from the Recombinant Holo-PYP and the Wild-Type Holo-PYP The laser flash photolysis and spectroscopy apparatus and the methods used for data analysis were as previously described (Meyer et al., 1987). The PYP sample was dialysed against a universal buffer (20 mM MES, 20 mM HEPES, and 20 mM glycine, pH 8.0) prior to the experiment. We used 1 ml samples, with an absorbance at 445 nm of approximately 0.2, for the kinetic measurements. By flashing the PYP sample with laser light of 440 nm, we could determine the kinetics of the light-induced absorbance changes. FIGS. 9a and 9b show the I1→I2 bleach reaction and the I2→P recovery of our in vivo formed holo-PYP. It can be seen that after a flash with 440 nm light, the PYP went through a normal photocycle. After fitting the data, we found that the kinetics of both the bleach and recovery reactions were similar to the wild-type PYP kinetics. The rate of recovery was 7.2 s$^{-1}$, compared to 6.3 s$^{-1}$ for wild-type and chemically reconstituted PYP (Meyer et al., 1987; Genick et al., 1997). The rate constant of the bleach was found to be 1.6 ms$^{-1}$. Since this is different from the 3.4 ms$^{-1}$ reported by Genick et al. (1997), we repeated the experiment under our conditions with native PYP and found the rate to be 1.3 ms$^{-1}$. This is approximately the same as what we measured with our recombinant PYP. The small differences in kinetics are not particularly significant since the kinetics have been shown to be sensitive to environmental effects (Meyer et al, 1987). The fact that the recombinant PYP is photoactive, with kinetics that resemble the wild-type, suggests that the PYP is correctly folded and is functional.

APPLICATIONS

As will be appreciated by a person skilled in the art, the current invention might be useful in the construction of an electro optical random access memory which uses a film of bacteriorhodopsin or a similar photochromic substance that can change between two light absorbing states in response to light of each of two wavelengths, as described in U.S. Pat. No. 5,228,001 to Birge et al. Thanks to its solubility and thermostability the PYP has been suggested as being a good alternative to bacteriorhodopsin as the photochromic substance (Hoff, 1995).

Further applications of the present invention include uses of the present invention in production of liquid crystal polymers, in biochips, and in light-inducible gene expression systems. More particularly, the present invention provides an economic and efficient way of producing para-hydroxycinnamic acid, using the TAL enzyme of the present invention. Efficient production of para-hydroxycinnamic acid can be of interest for the production of liquid crystal polymers for use in a variety of products, such as, but not limited to LCD screens.

TABLE 1

| Organism | Enzymatic properties | L-Tyrosine | L-Phenylalanine |
|---|---|---|---|
| Rhodobacter capsulatus | $K_M$ (μM) | 15.6 | 1277 |
| | $k_{cat}$ (s$^{-1}$) | 27.7 | 15.1 |
| | $k_{cat}/K_M$ | 1.77 | 0.0118 |
| Zea mays | $K_M$ (μM) | 19 | 270 |
| | $k_{cat}$ (s$^{-1}$) | 0.9 | 10 |
| | $k_{cat}$/Km | 0.0473 | 0.037 |
| Petroselinum crispum | $K_M$ (μM) | 2500 | 17.2 |
| | $k_{cat}$ (s$^{-1}$) | 0.3 | 22 |
| | $k_{cat}$/Km | 0.00012 | 1.28 |

Table 1 shows the comparison of the enzymatic properties for PAL and TAL. The KM and $k_{cat}$ values for the *Rhodobacter capsulatus* enzyme are the mean values of six independent measurements. The values for the maize enzyme are taken from Rösler et al. (1997), those from parsley are from Appert et al. (1994).

REFERENCES

Anson, J. G., Gilbert, H. J., Oram, J. D., and Minton, N. P. (1987) Gene 58, 189-199.
Appert, C., Logemann, E., Hahlbrock, K., Schmid, J., and Amrhein, N. (1994) Eur. J. Biochem. 225, 491-499.
Bandoni, R. J., Moore, K., Subba Rao, P. V., and Towers, G. H. N. (1968) Phytochemistry 7, 205-207.
Borgstahl, G. E. O., Williams, D. R., and Getzoff, E. D. (1995) Biochemistry 34, 6278-6287.
Campbell, M. M., and Sederoff, R. R. (1996) Plant Physiol. 110, 3-13.
Cramer (1989) Plant Mol. Biol. 12, 367-383.
Dixon, R. A., and Pavia, N. L. (1995) Plant Cell 7, 1085-1097.
Edwards (1985) Proc. Natl. Acad. Sci. USA 82, 6731-6735.
Ehlting, J., Büttner, D., Wang, Q., Douglas, C. J., Smossich, I. E., and Kombrink, E. (1999) The Plant Journal 19, 9-20.
Emes, A. V., and Vining, L. C. (1970) Can. J. Biochem. 48, 613-622.
Fulda, M., Heinz, E., and Wolter, F. P. (1994) Mol. Gen. Genet. 242, 241-249.
Genick, U. K., Devanathan, S., Meyer, T. E., Canestrelli, I. L., Williams, E., Cusanovich, M. A., Tollin, G., and Getzoff, E. D. (1997) Biochemistry 36, 8-14.
Genick, U. K., Soltis, S. M., Kuhn, P., Canestrelli, I. L., and Getzoff, E. D. (1998) Nature 392(6672), 206-209.
Gross, G. G., and Zenk, M. H. (1966) Z. Naturforschg. 21 b, 683-690.
Hahlbrock, K., and Scheel, D. (1989) Annu. Rev. Plant Physiol. Plant Mol. Biol. 40, 347-369.
Hoff, W. D. (1995) PhD thesis, University of Amsterdam, Amsterdam, The Netherlands. Imamoto, Y., Ito, T., Kataoka, M., and Tokunga, F. (1995) FEBS Lett. 374(2), 157-160.
Jiang, Z., Swem, L. R., Rushing, B. G., Devanathan, S., Tollin, G., and Bauer, C. E. (1999) Science 285(5426), 406-409.

Knobloch, K. H., Hahlbrock, K. (1977) Arch. Biochem. Biophys. 184, 237-248.
Koh, M., van Driessche, G., Samyn, B., Hoff, W. D., Meyer, T. E., Cusanovich, M. A., and Van Beeumen, J. J. (1996) Biochemistry 35, 2526-2534.
Kort, R., Hoff, W. D., van West, M., Kroon, A. R., Hoffer, S. M., Vlieg, K. H., Crielaard, W., Van Beeumen, J. J., and Hellingwerf, K. J. (1996) EMBO J. 15, 3209-3218.
Kort, R., Phillips-Jones, M. K., van Aalten, D. M., Haker, A., Hoffer, S. M., Hellingwerf, K. J., and Crielaard, W. (1998) Biochim. Biophys. Acta 1385(1), 1-6.
Koukol, J., and Conn, E. E. (1961) J. Biol. Chem. 236, 2692-2698.
Kyndt, J. A., Meyer, T. E., Cusanovich, M. A., and Van Beeumen, J. J. (2002) FEBS Lett. 512, 240-244.
Lindl, T., Kreuzaler, F., and Hahlbrock, K. (1972) Biochim. Biophys. Acta 66857, 458-464.
Louis, R., Dietrich, A., Hahlbrock, K., and Schulz, W. (1989) EMBO J. 8, 1641-1648.
Meyer, T. E. (1985) Biochem. Biophys. Acta 806, 175-183.
Meyer, T. E. Yakali, E., Cusanovich, M. A., and Tollin, G. (1987) Biochemistry 26, 418-423.
Minami, E., Ozeki, Y., Matsouka, M, Kiozuka, N., and Tanaka, Y. (1989) Eur. J. Biochem. 185, 19-25.
Obel, N., and Scheller, H. V. (2000) Anal. Biochem. 286, 38-44.
Ogata (1967) Agric. Biol. Chem. 31, 200-206.
Perman, B., Srajer, V., Ren, Z., Teng, T., Pradervand, C., Ursly, T., Bourgois, D., Schotte, F., Wulff, M., Kort, R., Hellingwerf, K., and Moffat, K. (1998) Science 279 (5358), 1946-1950.
Rasmussen, O. F., and Oerum, H. (1991) DNA Sequence 1, 207-211.
Rösler, J., Krekel, F., Amrhein, N., and Schmid, J. (1997) Plant Physiol. 113, 175-179.
Sambrook, J., Fritsch, E. F., and Maniatis, T. (1989) Cold spring Harbor Laboratory Press.
Schwede, T. F., Rétey, J., and Schulz, G. E. (1999) Biochemistry 38, 5355-5361.
Sprenger, W. W., Hoff, W. D., Armitage, J. P., and Hellingwerf, K. J. (1993) J. Bacteriol. 175, 3096-3104.
Ujj, L., Devanathan, S., Meyer, T. E., Cusanovich, M. A., Tollin, G., Atkinson, G. H. (1998) Biophys. J. 75(1), 406-412.
Van Beeumen, J. J., Devreese, B., Van Bun, S., Hoff, W. D., Hellingwerf, K. J., Meyer, T. E., McRee, D. E., and Cusanovich, M. A. (1993) Protein Sci. 2, 1114-1125.

The invention claimed is:

1. A recombinant vector comprising a nucleotide sequence encoding a tyrosine-ammonium lyase (TAL) polypeptide having the sequence of SEQ ID NO:4 or a sequence having at least 95% sequence identity therewith, said polypeptide having a catalytic efficiency for L-tyrosine which is at least 10 times higher for L-tyrosine than for L-phenylalanine.

2. The vector according to claim 1, wherein said nucleotide sequence encoding TAL is a bacterial nucleotide sequence.

3. The vector according to claim 1, wherein said nucleotide sequence encoding TAL is derived from *Rhodobacter*.

4. The vector according to claim 3, wherein said nucleotide sequence encoding TAL is derived from *Rhodobacter capsulatus*.

5. An isolated nucleic acid sequence comprising SEQ ID NO:3, or a sequence having at least 95% sequence identity with SEQ ID NO:3, said isolated nucleic acid encoding a protein having tyrosine ammonilyase activity, or the complement thereof.

6. The nucleic acid sequence according to claim 5, which is DNA, cDNA, genomic DNA or RNA wherein T is replaced by U.

7. The nucleic acid sequence of claim 5, encoding a protein as defined in SEQ ID NO: 4.

8. An isolated host cell comprising the vector of claim 1.

9. An isolated host cell comprising the nucleic acid sequence according to claim 5.

10. An isolated host cell comprising the nucleic acid according to claim 7.

11. The vector according to claim 1, wherein said nucleotide sequence encoding a TAL polypeptide is operably linked to at least one control sequence allowing the expression of said nucleotide sequence in prokaryotic and/or eukaryotic host cells.

12. The vector according to claim 1, further comprising a nucleotide sequence encoding a p-hydroxycinnamyl:CoA ligase (pCL) polypeptide.

13. The vector according to claim 12, further comprising a nucleotide sequence encoding a photoactive yellow protein.

14. The isolated host cell according to claim 8, further comprising a nucleotide sequence encoding a p-hydroxycinnamyl:CoA ligase (pCL) polypeptide.

15. The isolated host cell according to claim 14, wherein said nucleotide sequence encoding said a TAL polypeptide and said nucleotide sequence encoding a pCL polypeptide are present together as a dual biosynthetic gene operon.

16. The isolated host cell according to claim 15, wherein said dual biosynthetic gene operon is under the control of an inducible promoter sequence.

17. The isolated host cell according to claim 16, wherein said inducible promoter is an inducible tac promoter.

18. The isolated host cell according to claim 14, wherein said nucleotide sequence encoding said a TAL polypeptide and said nucleotide sequence encoding a pCL polypeptide are present in separate gene constructs.

19. The isolated host cell according to claim 14, further comprising a nucleotide sequence encoding a photoactive yellow protein.

20. The isolated host cell according to claim 14, which naturally expresses a PYP protein.

* * * * *

UNITED STATES PATENT AND TRADEMARK OFFICE
CERTIFICATE OF CORRECTION

PATENT NO. : 7,241,611 B2  Page 1 of 1
APPLICATION NO. : 10/464609
DATED : July 10, 2007
INVENTOR(S) : Kyndt et al.

It is certified that error appears in the above-identified patent and that said Letters Patent is hereby corrected as shown below:

Column 31, Line 49, replace "ammoilyase" with --ammonia lyase-- .

Signed and Sealed this

Twenty-first Day of August, 2007

JON W. DUDAS
*Director of the United States Patent and Trademark Office*

UNITED STATES PATENT AND TRADEMARK OFFICE
CERTIFICATE OF CORRECTION

PATENT NO. : 7,241,611 B2  Page 1 of 1
APPLICATION NO. : 10/464609
DATED : July 10, 2007
INVENTOR(S) : Kyndt et al.

It is certified that error appears in the above-identified patent and that said Letters Patent is hereby corrected as shown below:

Column 31, Line 49, replace "ammonilyase" with --ammonia lyase--.

This certificate supersedes the Certificate of Correction issued August 21, 2007.

Signed and Sealed this

Third Day of June, 2008

JON W. DUDAS
*Director of the United States Patent and Trademark Office*

SEQUENCE LISTING

<160> NUMBER OF SEQ ID NOS: 13

<210> SEQ ID NO 1
<211> LENGTH: 375
<212> TYPE: DNA
<213> ORGANISM: Halorhodospira halophila

<400> SEQUENCE: 1

```
atggaaatca ttccgttcgg gacgaacgac atcgacaaca tcctggcgcg cgagcccgcg      60
cgtgcggaaa gcctgccgtt cggcgccgtg cttctcgacc gcatggggcg gatcgccaaa     120
tacaacaagg ccgaggggct gatcgcgggc cgcgatccct cgacggtgat cggccgcgat     180
ttcttcaacg agatcgcgcc ctgcgccaag ggcaagcggt tccacgggga attcctgaaa     240
ttcaaccgca ccggccaggc caatgtgatg ctggactaca agttcaatta caagggcgcc     300
gaagtggcgg tgaagatcca cctcaagtcc caacccgacg gccagttctg ctggctcttc     360
gtgaagcggg cctga                                                      375
```

<210> SEQ ID NO 2
<211> LENGTH: 124
<212> TYPE: PRT
<213> ORGANISM: Halorhodospira halophila

<400> SEQUENCE: 2

```
Met Glu Ile Ile Pro Phe Gly Thr Asn Asp Ile Asp Asn Ile Leu Ala
 1               5                  10                  15

Arg Glu Pro Ala Arg Ala Glu Ser Leu Pro Phe Gly Ala Val Leu Leu
            20                  25                  30

Asp Arg Met Gly Arg Ile Ala Lys Tyr Asn Lys Ala Glu Gly Leu Ile
        35                  40                  45

Ala Gly Arg Asp Pro Ser Thr Val Ile Gly Arg Asp Phe Phe Asn Glu
    50                  55                  60

Ile Ala Pro Cys Ala Lys Gly Lys Arg Phe His Gly Glu Phe Leu Lys
65                  70                  75                  80
```

Phe Asn Arg Thr Gly Gln Ala Asn Val Met Leu Asp Tyr Lys Phe Asn
            85                  90                  95

Tyr Lys Gly Ala Glu Val Ala Val Lys Ile His Leu Lys Ser Gln Pro
            100                 105                 110

Asp Gly Gln Phe Cys Trp Leu Phe Val Lys Arg Ala
            115                 120

<210> SEQ ID NO 3
<211> LENGTH: 1626
<212> TYPE: DNA
<213> ORGANISM: Rhodobacter capsulatus
<220> FEATURE:
<221> NAME/KEY: misc_feature
<222> LOCATION: (1)...(1623)
<223> OTHER INFORMATION: n = A,T,C or G

<400> SEQUENCE: 3

```
atgctcgatg caaccatcgg agaaagcgg atgaccctgc agtcacagac ggccaaggac    60
tgcctcgcgc tggacggggc gctgacactt gtccaatgcg aggccatcgc gacacatcgc   120
agccggattt cggtgacccc cgcgctgcgc gagcgctgcg cgcgggccca tgcccggctt   180
gagcacgcca tcgccgagca gcgccacatt tacggcatca ccaccggctt cggcccgctg   240
gcgaaccgtc tgatcggggc cgatcagggg gcggagctgc agcagaacct gatctatcat   300
ctggccaccg gcgtcgggcc gaaactgagc tgggccgagg cgcgggcgtt gatgctggcg   360
cggctcaact cgatcctgca aggcgcgtcg ggggcctcgc cggagacgat cgaccggatc   420
gttgcggtgc tcaatgcggg gttttgccccc gaggttccgg cgcagggaac ggtgggcgcc   480
tcgggcgatc tgaccccgct tgcgcatatg gtgctggcgc tgcagggacg ggggcggatg   540
atcgacccct cggccgcgt gcaggaggcc ggggcggtga tggatcggct ctgcggcggt   600
ccgctgacgc tggcggcccg tgacgggctg gcgctggtga atggcacctc ggcgatgacc   660
gcgattgcgg ccctgaccgg ggtcgaggcg gcgcgggcga tcgacgccgc gcttcggcac   720
agcgcggtcc tgatggaggt cttgtccggt catgccgaag cctggcatcc ggctttcgca   780
gagctgcgcc cgcatccggg gcagctgcgg gcgaccgagc ggctggcgca ggcgctggat   840
ggggcggggc gggtctgtcg gaccctgacc gcggcgcggc ggctgaccgc gcggatctg    900
cggcccgaag atcatccggc gcaggatgcc tacagtctgc gcgtggtgcc gcaactggtc   960
ggcgcggtct gggacacgct ggactggcac gatcgtgtcg tcacctgcga gctcaattcc  1020
gtcaccgaca atccgatctt tcccgagggc tgcgcggtgc ccgccctgca cggcggcaat  1080
ttcatgggcg tgcatgtcgc ccttgcctcc gatgcgctga acgcggcgct ggtgacgctg  1140
gcgggcctgg tcgagcgtca gatcgcccgg ctgaccgacg aaaagctgaa caagggcctg  1200
cccgccttcc tgcacggggg gcaggcgggg ctgcaatcgg gcttcatggg ggcgcaggtc  1260
acggcgacgc gcttctggcc ggaaatgcgg gcgaatgcca cgccggtttc ggtgcagtcg  1320
ctgtcgacca atggcgccaa tcaggatgtg gtctcgatgg aacgattgc cgcgcggagg  1380
gcgcgggcgc agctgctgcc cctgtcgcag atccaggcga tcctggcgct tgcccttgcc  1440
caggcgatgg atctgcttga cgaccccgag gggcaggccg gatggtcgct tacggcgcgg  1500
gatctgcggg accggatccg gcggtctcg cccgggcttc gcgccgacag accgcttgcc  1560
ggggatatcg aagcggtggc acagggtctg cgtcatccct ccnnngccgc cgatcccccg  1620
gcatga                                                              1626
```

<210> SEQ ID NO 4
<211> LENGTH: 540
<212> TYPE: PRT
<213> ORGANISM: Rhodobacter capsulatus

<400> SEQUENCE: 4

```
Met Leu Asp Ala Thr Ile Gly Arg Lys Arg Met Thr Leu Gln Ser Gln
 1               5                  10                  15

Thr Ala Lys Asp Cys Leu Ala Leu Asp Gly Ala Leu Thr Leu Val Gln
            20                  25                  30

Cys Glu Ala Ile Ala Thr His Arg Ser Arg Ile Ser Val Thr Pro Ala
        35                  40                  45

Leu Arg Glu Arg Cys Ala Arg Ala His Ala Arg Leu Glu His Ala Ile
    50                  55                  60

Ala Glu Gln Arg His Ile Tyr Gly Ile Thr Thr Gly Phe Gly Pro Leu
65                  70                  75                  80

Ala Asn Arg Leu Ile Gly Ala Asp Gln Gly Ala Glu Leu Gln Gln Asn
                85                  90                  95

Leu Ile Tyr His Leu Ala Thr Gly Val Gly Pro Lys Leu Ser Trp Ala
            100                 105                 110

Glu Ala Arg Ala Leu Met Leu Ala Arg Leu Asn Ser Ile Leu Gln Gly
        115                 120                 125

Ala Ser Gly Ala Ser Pro Glu Thr Ile Asp Arg Ile Val Ala Val Leu
    130                 135                 140

Asn Ala Gly Phe Ala Pro Glu Val Pro Ala Gln Gly Thr Val Gly Ala
145                 150                 155                 160

Ser Gly Asp Leu Thr Pro Leu Ala His Met Val Leu Ala Leu Gln Gly
                165                 170                 175

Arg Gly Arg Met Ile Asp Pro Ser Gly Arg Val Gln Glu Ala Gly Ala
            180                 185                 190

Val Met Asp Arg Leu Cys Gly Gly Pro Leu Thr Leu Ala Ala Arg Asp
        195                 200                 205

Gly Leu Ala Leu Val Asn Gly Thr Ser Ala Met Thr Ala Ile Ala Ala
    210                 215                 220

Leu Thr Gly Val Glu Ala Ala Arg Ala Ile Asp Ala Ala Leu Arg His
225                 230                 235                 240

Ser Ala Val Leu Met Glu Val Leu Ser Gly His Ala Glu Ala Trp His
                245                 250                 255

Pro Ala Phe Ala Glu Leu Arg Pro His Pro Gly Gln Leu Arg Ala Thr
            260                 265                 270

Glu Arg Leu Ala Gln Ala Leu Asp Gly Ala Gly Arg Val Cys Arg Thr
        275                 280                 285

Leu Thr Ala Ala Arg Arg Leu Thr Ala Ala Asp Leu Arg Pro Glu Asp
    290                 295                 300

His Pro Ala Gln Asp Ala Tyr Ser Leu Arg Val Val Pro Gln Leu Val
305                 310                 315                 320

Gly Ala Val Trp Asp Thr Leu Asp Trp His Asp Arg Val Val Thr Cys
                325                 330                 335

Glu Leu Asn Ser Val Thr Asp Asn Pro Ile Phe Pro Glu Gly Cys Ala
            340                 345                 350

Val Pro Ala Leu His Gly Gly Asn Phe Met Gly Val His Val Ala Leu
        355                 360                 365

Ala Ser Asp Ala Leu Asn Ala Ala Leu Val Thr Leu Ala Gly Leu Val
    370                 375                 380
```

-continued

```
Glu Arg Gln Ile Ala Arg Leu Thr Asp Glu Lys Leu Asn Lys Gly Leu
385                 390                 395                 400

Pro Ala Phe Leu His Gly Gly Gln Ala Gly Leu Gln Ser Gly Phe Met
            405                 410                 415

Gly Ala Gln Val Thr Ala Thr Ala Leu Leu Ala Glu Met Arg Ala Asn
                420                 425                 430

Ala Thr Pro Val Ser Val Gln Ser Leu Ser Thr Asn Gly Ala Asn Gln
            435                 440                 445

Asp Val Val Ser Met Gly Thr Ile Ala Ala Arg Arg Ala Arg Ala Gln
450                 455                 460

Leu Leu Pro Leu Ser Gln Ile Gln Ala Ile Leu Ala Leu Ala Leu Ala
465                 470                 475                 480

Gln Ala Met Asp Leu Leu Asp Asp Pro Glu Gly Gln Ala Gly Trp Ser
                485                 490                 495

Leu Thr Ala Arg Asp Leu Arg Asp Arg Ile Arg Ala Val Ser Pro Gly
                500                 505                 510

Leu Arg Ala Asp Arg Pro Leu Ala Gly Asp Ile Glu Ala Val Ala Gln
            515                 520                 525

Gly Leu Arg His Pro Ser Ala Ala Asp Pro Pro Ala
530                 535                 540
```

<210> SEQ ID NO 5
<211> LENGTH: 1398
<212> TYPE: DNA
<213> ORGANISM: Rhodobacter capsulatus

<400> SEQUENCE: 5

```
atgtgcgtcc gcaggcgaag ctgggcgggg ccgggctgtc ggcggcagag ctttacggtc      60
aggcgctcga attgcaggcg cgcattgccg ccgtccggca gcattacgcc gcgcttctgg     120
gcgagttcct ttatgaactc gacgatgcct gaggtccggc gcgccggctc cggggccttg     180
tcgcccccgg ccccggcc ggacggcctc ggcgcggtcc tgccacaagc ccccgacgcc       240
gcgatggtgc gccgtcttct gatcagcctg atccgcgccg aggcccggcg cgggcgcaac     300
cagatcctgc ccgaagccgc cttcaccggc gatccgcgca tcgacgagga gggtctcggc     360
ttcgactcgc tcgcccggct cgacctgatc ggggcggtgc gcgatttctt cgacctctcc     420
cgcaccggga tcgaggatta cgtctatgtc gaaccgaccc tgcagggctg gatcgaccgg     480
atcatgcagc atttcgacct tctggccgcc cggtccgaaa ccgcgcaggc ggtgtttcgc     540
acctccggat cgaccggcac gccaaagccg atcccgcatc cctggccgaa gctgatgcgc     600
gaagccgcca gcatggcccg cgatcagggc ctcgtccccg cgccggcgg cgcggtgatc      660
gggctcgttc ccgcgcacca cctgttcggc tgcctgttca cggcgcttct gccagaactc     720
gcaggtgcgg ccctgcgcga tctgaccgcc gcgccgcccg cctcggcgct gcgcacggcg     780
cagcccggcg atctgatcat cgccacgccg catctttggg cgcatctggg gcggccgga      840
gccttcccgc ccggtctgcg cggggtcagt tccggtgcgc cgatgcccga cgcgctgtgg     900
cacagcctgc ttgcgcagg gcttgaggat ctgaccgagg tctatggcgc ctcggaaacc      960
ggcggcatcg gcctgcgcag ggccccggc gccgctttca ccctgctgcc gttcctgtcc     1020
cgcagcgccc atgacgggat ttccgacggc ccgccccct tgccgctgca ggatcggctg     1080
cgctggaccg ggccggtccg cttcgtgatc gagggacgcc tcgatcaggc gctgcaggtc    1140
ggcggcgtca atgccgtct gggacatgtg aaatccgtgc tggaagccga gcccggggtc    1200
gaggcgcttg cgctgcggct tggcggcgac cggctgaagg ctttcgtggt ctgcgccgcc    1260
```

```
gatgcggaag ccgggctgga ggcgcggctg cgtgcccgcg ccgaagccgg gcttgacgcc    1320
ccggcgcggc cgcaacacta tcgcttcggt cgcgccctgc cgctgacccg cgaaggcaag    1380
gcccgggatt gggactga                                                  1398
```

<210> SEQ ID NO 6
<211> LENGTH: 465
<212> TYPE: PRT
<213> ORGANISM: Rhodobacter capsulatus

<400> SEQUENCE: 6

```
Met Cys Val Arg Arg Ser Trp Ala Gly Pro Gly Cys Arg Arg Gln
1               5                   10                  15

Ser Phe Thr Val Arg Arg Ser Asn Cys Arg Arg Ala Leu Pro Pro Ser
                20                  25                  30

Gly Ser Ile Thr Pro Arg Phe Trp Ala Ser Ser Phe Met Asn Ser Thr
            35                  40                  45

Met Pro Glu Val Arg Arg Ala Gly Ser Gly Ala Leu Ser Pro Pro Ala
        50                  55                  60

Pro Gly Pro Asp Gly Leu Gly Ala Val Leu Pro Gln Ala Pro Asp Ala
65                  70                  75                  80

Ala Met Val Arg Arg Leu Leu Ile Ser Leu Ile Arg Ala Glu Ala Arg
                85                  90                  95

Arg Gly Arg Asn Gln Ile Leu Pro Glu Ala Ala Phe Thr Gly Asp Pro
            100                 105                 110

Arg Ile Asp Glu Glu Gly Leu Gly Phe Asp Ser Leu Ala Arg Leu Asp
        115                 120                 125

Leu Ile Gly Ala Val Arg Asp Phe Phe Asp Leu Ser Arg Thr Gly Ile
    130                 135                 140

Glu Asp Tyr Val Tyr Val Glu Pro Thr Leu Gln Gly Trp Ile Asp Arg
145                 150                 155                 160

Ile Met Gln His Phe Asp Leu Leu Ala Ala Arg Ser Glu Thr Ala Gln
                165                 170                 175

Ala Val Phe Arg Thr Ser Gly Ser Thr Gly Thr Pro Lys Pro Ile Pro
            180                 185                 190

His Pro Trp Pro Lys Leu Met Arg Glu Ala Ala Ser Met Ala Arg Asp
        195                 200                 205

Gln Gly Leu Val Pro Ala Pro Gly Gly Ala Val Ile Gly Leu Val Pro
    210                 215                 220

Ala His His Leu Phe Gly Cys Leu Phe Thr Ala Leu Leu Pro Glu Leu
225                 230                 235                 240

Ala Gly Ala Ala Leu Arg Asp Leu Thr Ala Ala Pro Ala Ser Ala
                245                 250                 255

Leu Arg Thr Ala Gln Pro Gly Asp Leu Ile Ile Ala Thr Pro His Leu
            260                 265                 270

Trp Ala His Leu Gly Ala Ala Gly Ala Phe Pro Pro Gly Leu Arg Gly
        275                 280                 285

Val Ser Ser Gly Ala Pro Met Pro Asp Ala Leu Trp His Ser Leu Leu
    290                 295                 300

Ala Ala Gly Leu Glu Asp Leu Thr Glu Val Tyr Gly Ala Ser Glu Thr
305                 310                 315                 320

Gly Gly Ile Gly Leu Arg Arg Ala Pro Gly Ala Ala Phe Thr Leu Leu
                325                 330                 335

Pro Phe Leu Ser Arg Ser Ala Asp Asp Gly Ile Ser Asp Gly Pro Ala
```

-continued

```
              340                 345                 350
Pro Leu Pro Leu Gln Asp Arg Leu Arg Trp Thr Gly Pro Val Arg Phe
            355                 360                 365
Val Ile Glu Gly Arg Leu Asp Gln Ala Leu Gln Val Gly Gly Val Asn
        370                 375                 380
Val Arg Leu Gly His Val Lys Ser Val Leu Glu Ala Glu Pro Gly Val
385                 390                 395                 400
Glu Ala Leu Ala Leu Arg Leu Gly Gly Asp Arg Leu Lys Ala Phe Val
                405                 410                 415
Val Cys Ala Ala Asp Ala Glu Ala Gly Leu Glu Ala Arg Leu Arg Ala
            420                 425                 430
Arg Ala Glu Ala Gly Leu Asp Ala Pro Ala Arg Pro Gln His Tyr Arg
        435                 440                 445
Phe Gly Arg Ala Leu Pro Leu Thr Arg Glu Gly Lys Ala Arg Asp Trp
    450                 455                 460
Asp
465
```

<210> SEQ ID NO 7
<211> LENGTH: 23
<212> TYPE: DNA
<213> ORGANISM: Artificial Sequence
<220> FEATURE:
<223> OTHER INFORMATION: Primer

<400> SEQUENCE: 7
cggaattcat gctcgatgca acc        23

<210> SEQ ID NO 8
<211> LENGTH: 25
<212> TYPE: DNA
<213> ORGANISM: Artificial Sequence
<220> FEATURE:
<223> OTHER INFORMATION: Primer

<400> SEQUENCE: 8
gcccaagctt tcatgccggg ggatc       25

<210> SEQ ID NO 9
<211> LENGTH: 29
<212> TYPE: DNA
<213> ORGANISM: Artificial Sequence
<220> FEATURE:
<223> OTHER INFORMATION: Primer

<400> SEQUENCE: 9
acatgcatgc ggaagctgtg gtatggctg     29

<210> SEQ ID NO 10
<211> LENGTH: 25
<212> TYPE: DNA
<213> ORGANISM: Artificial Sequence
<220> FEATURE:
<223> OTHER INFORMATION: Primer

<400> SEQUENCE: 10
gcccaagctt tcatgccggg ggatc       25

<210> SEQ ID NO 11
<211> LENGTH: 25
<212> TYPE: DNA
<213> ORGANISM: Artificial Sequence

```
<220> FEATURE:
<223> OTHER INFORMATION: Primer

<400> SEQUENCE: 11
cggaattcat gaactcgacg atgcc                                          25

<210> SEQ ID NO 12
<211> LENGTH: 23
<212> TYPE: DNA
<213> ORGANISM: Artificial Sequence
<220> FEATURE:
<223> OTHER INFORMATION: Primer

<400> SEQUENCE: 12
cgcaagcttc agtcccaatc ccg                                            23

<210> SEQ ID NO 13
<211> LENGTH: 31
<212> TYPE: DNA
<213> ORGANISM: Artificial Sequence
<220> FEATURE:
<223> OTHER INFORMATION: Primer

<400> SEQUENCE: 13
tcccaagctt gtggaattgt gagcggataa c                                   31
```